US008299241B2

(12) United States Patent
Gharbaoui et al.

(10) Patent No.: US 8,299,241 B2
(45) Date of Patent: Oct. 30, 2012

(54) PROCESSES FOR PREPARING (R)-8-CHLORO-1-METHYL-2,3,4,5-TETRAHYDRO-1H-3-BENZAZEPINE AND INTERMEDIATES THEREOF

(75) Inventors: Tawfik Gharbaoui, Escondido, CA (US); Sagun K. Tandel, San Diego, CA (US); You-An Ma, Poway, CA (US); Marlon Carlos, Chula Vista, CA (US); John Robert Fritch, Ramona, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 364 days.

(21) Appl. No.: 12/517,625

(22) PCT Filed: Dec. 4, 2007

(86) PCT No.: PCT/US2007/024900
§ 371 (c)(1),
(2), (4) Date: Jan. 4, 2010

(87) PCT Pub. No.: WO2008/070111
PCT Pub. Date: Jun. 12, 2008

(65) Prior Publication Data
US 2010/0305316 A1    Dec. 2, 2010

Related U.S. Application Data

(60) Provisional application No. 60/873,036, filed on Dec. 5, 2006.

(51) Int. Cl.
C07C 233/22    (2006.01)
C07C 231/02    (2006.01)
C07C 209/50    (2006.01)
C07D 263/10    (2006.01)
C07D 223/16    (2006.01)

(52) U.S. Cl. ........ 540/594; 548/239; 564/133; 564/139; 564/142; 564/182; 564/414

(58) Field of Classification Search .................. 540/594; 564/133, 139, 142, 182, 414; 548/239
See application file for complete search history.

(56) References Cited

U.S. PATENT DOCUMENTS

| | | |
|---|---|---|
| 2,900,415 A | 8/1959 | Biel et al. |
| 3,652,543 A | 3/1972 | Hoegerle |
| 3,716,639 A | 2/1973 | Hoegerle et al. |
| 4,108,989 A | 8/1978 | Holden |
| 4,111,957 A | 9/1978 | Holden et al. |
| 4,210,749 A | 7/1980 | Shetty |
| 4,233,217 A | 11/1980 | Shetty |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,856,503 A | 1/1999 | Aebi et al. |
| 5,861,393 A | 1/1999 | Danilewicz et al. |
| 5,925,651 A | 7/1999 | Hutchinson |
| 5,939,415 A | 8/1999 | Laufer et al. |
| 5,942,535 A | 8/1999 | Laufer et al. |
| 5,958,943 A | 9/1999 | Laufer et al. |
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,514,422 B2 | 4/2009 | Smith et al. |
| 7,704,993 B2 | 4/2010 | Smith et al. |
| 7,977,329 B2 | 7/2011 | Smith et al. |
| 8,168,624 B2 | 5/2012 | Agarwal et al. |
| 2009/0143576 A1 | 6/2009 | Weigl et al. |
| 2010/0004223 A1 | 1/2010 | Agarwal et al. |
| 2010/0173894 A1 | 7/2010 | Brian et al. |

FOREIGN PATENT DOCUMENTS

| | | |
|---|---|---|
| AU | 515236(B2) | 3/1981 |
| CA | 1090797 | 12/1980 |
| CA | 2197789 | 8/1995 |
| CH | 500194 | 1/1971 |
| DE | 1944121 | 3/1970 |
| DE | 1914456 | 6/1971 |
| DE | 3315106 A1 | 11/1983 |
| DE | 3418270 | 11/1985 |
| EP | 0007070 | 1/1980 |
| EP | 27695 | 10/1983 |
| EP | 0096838 | 12/1983 |
| EP | 0161350 | 11/1985 |

(Continued)

OTHER PUBLICATIONS

U.S. Appl. No. 60/372,058, filed Apr. 12, 2002, Arena Pharmaceuticals.
U.S. Appl. No. 60/405,495, filed Aug. 23, 2002, Arena Pharmaceuticals.
U.S. Appl. No. 60/434,607, filed Dec. 18, 2002, Arena Pharmaceuticals.
U.S. Appl. No. 60/479,280, filed Jun. 17, 2003, Arena Pharmaceuticals.
U.S. Appl. No. 60/512,967, filed Oct. 21, 2003, Arena Pharmaceuticals.
U.S. Appl. No. 60/638,221, filed Dec. 21, 2004, Arena Pharmaceuticals.
U.S. Appl. No. 60/789,191, filed Apr. 3, 2006, Arena Pharmaceuticals.
U.S. Appl. No. 60/873,036, filed Dec. 5, 2006, Arena Pharmaceuticals.

(Continued)

Primary Examiner — Brenda Coleman
(74) Attorney, Agent, or Firm — Foley & Lardner LLP

(57) ABSTRACT

The present invention provides processes and intermediates for the preparation of (R)-8-chloro-1-methyl-2,3,4,5-tetrahydro-1H-3-benzazepine and salts thereof which are useful as serotonin-2C (5-HT2C) receptor agonists for the treatment of, for example, obesity.

66 Claims, No Drawings

FOREIGN PATENT DOCUMENTS

| | | |
|---|---|---|
| EP | 0174118 | 3/1986 |
| EP | 0080779 | 7/1986 |
| EP | 0204349 | 12/1986 |
| EP | 0285287 | 10/1988 |
| EP | 0285287 A3 | 8/1990 |
| EP | 0285919 B1 | 10/1994 |
| EP | 0987235 A1 | 3/2000 |
| EP | 1074549 | 2/2001 |
| EP | 1074549 | 11/2003 |
| EP | 1838677 | 9/2009 |
| FR | 2518544 | 6/1983 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1542317 | 3/1979 |
| GB | 1599705 | 10/1981 |
| GB | 2133401 | 7/1984 |
| JP | 5339263 | 12/1993 |
| JP | 06298746 | 10/1994 |
| JP | 08134048 | 5/1996 |
| JP | 09030960 | 2/1997 |
| JP | 90987258 | 3/1997 |
| NL | 7807819 | 1/1980 |
| SU | 1238732 A3 | 6/1986 |
| WO | WO 2008807858 | 10/1988 |
| WO | WO 9119698 | 12/1991 |
| WO | WO 9300094 | 1/1993 |
| WO | WO 9316997 | 9/1993 |
| WO | WO 9513274 | 5/1995 |
| WO | WO 9604271 | 2/1996 |
| WO | WO 9605194 | 2/1996 |
| WO | WO 9633993 | 10/1996 |
| WO | WO 9724364 A1 | 7/1997 |
| WO | WO 9806701 | 2/1998 |
| WO | WO 9840385 | 9/1998 |
| WO | WO 0274746 | 3/2002 |
| WO | WO 0240471 | 5/2002 |
| WO | WO 0248124 A2 | 6/2002 |
| WO | WO 02074746 A1 | 9/2002 |
| WO | WO 03000663 A1 | 1/2003 |
| WO | WO 03027068 A2 | 4/2003 |
| WO | WO 03062392 A2 | 7/2003 |
| WO | WO 03086306 A2 | 10/2003 |
| WO | WO 03086306 A3 | 2/2004 |
| WO | WO 2004037788 | 5/2004 |
| WO | WO 2005003096 A1 | 1/2005 |
| WO | WO 2005019179 A2 | 3/2005 |
| WO | WO 2005042490 A1 | 5/2005 |
| WO | WO 2006013209 A2 | 2/2006 |
| WO | WO 2006043710 A1 | 4/2006 |
| WO | WO 2006069363 A2 | 6/2006 |
| WO | WO 2006071740 A2 | 7/2006 |
| WO | WO 20060069363 A3 | 5/2007 |
| WO | WO 2007120517 A3 | 10/2007 |
| WO | WO 2008070111 A3 | 8/2008 |
| WO | WO 2009111004 | 9/2009 |
| WO | WO 2010148207 | 12/2010 |

OTHER PUBLICATIONS

U.S. Appl. No. 61/068,102, filed Mar. 4, 2008, Arena Pharmaceuticals.

U.S. Appl. No. 61/268,930, filed Jun. 18, 2009, Arena Pharmaceuticals.

U.S. Appl. No. 12/921,101, filed Oct. 4, 2010, Arena Pharmaceuticals.

U.S. Appl. No. 13/309,497, filed Dec. 1, 2011, Arena Pharmaceuticals.

U.S. Appl. No. 13/378,797, filed Feb. 15, 2012, Arena Pharmaceuticals.

U.S. Appl. No. 13/425,699, filed Mar. 21, 2012, Arena Pharmaceuticals.

Hazebroucq, "Acces A Des 1-H, Tetrahydro-2, 3, 4,5 Benzazepines-3 One-1 Et A Des Hexahydro Imidazo Isoquinoleines", Ann. Chim., t.l:22 1-54 (1966) French Lang Only.

"Remington's Pharmaceutical Sciences" 17th ed., Mack Publishing Company, Easton Pa.: 1418 (1985).

Baindur, et al., "(±)-3-Allyl-7-halo-8-hydroxy-1-phenyl-2,3,4,5-tetrahydro-1H-3-Benzazepines As Selective High Affinity Di Dopamine Receptor Antagonists: Synthesis and Structure-Activity Relationship", J. Med. Chem., 35:67-72 (1992).

Barnes, "Pharmacological Strategies for Relapse Prevention in Schizophrenia," Psychiatry 3(10): 37-40 (2004).

Ben Hassine-Coniac, et al., "Preparation et Proprietes D'aldehydes Dans La Serie De La Benzazepine-3", Bulletin de La Societe Chimique de France, 11:3985-92 (1971) French lang only.

Biel, et al. Bronchodilators, N-Substituted Derivatives of 1-(3',4'-Dihydroxyphenyl)-2-aminoethanol (Artenerol), J. Am. Chem. Soc. 1954, vol. 76, pp. 3149-3153.

Bosch, et al., "Studies on the Synthesis of Pentacyclic Strychnos Indole Alkaloids. Photocyclization of N-Chloroacetyl-1,2,3,4,5,6-hexahydro-1,5-methanoazocino [4,3-b] Indole Derivatives", Tetrahedron, 41(12):2557-66 (1985).

Bremner, "Seven Membered Rings", Institute for Biomolecular Science, Dept. of Chemistry, University of Wollongong; "Progress in Heterocyclic Chemistry 13", Pergamon Press, Ch. 7:340-77 (2001).

Casy, et al., "Some Arylalkylamino Analogs of Acyclic Analgetics", J Med Chem., (1968) 11(3):599-601.

Chang, et al., "Dopamine Receptor Binding Properties of Some 2,3,4,5-Tetrahydro-1H-3-Benzazepine-7-ols With Non-Aromatic Substituents in the 5-Position", Bioorganic & Medicinal Chemistry Letters, 2(5):399-402 (1992).

Chumpradit, et al., "(±)-7-Chloro-8-hydroxyl-l-(4'-[$^{125}$I]iodophenyl)-3-methyl-2,3,4,5-tetrahydro-1H-3-benzazepine: A Potential CNS D-1 Dopamine Receptor Imaging Agent", J. Med. Chem., 32:1431-5 (1989).

Clark, et al., "1,9-Alkano-Bridged 2,3,4,5-Tetrahydro-1H-3-benzazepines With Affinity for the A$_2$-Adrenoceptor and the 5-HT1A Receptor", J. Med. Chem., 33:633-41 (1990).

Deady, et al., "Synthesis of Some Tetrahydro-2-and 3-Benzazepines, and of Hexahydro-3-Benzazocine", JCS Perkin 1,782-3 (1973).

DeMarinis et al., "Development of an Affinity Ligand for Purification of A2-Adrenoceptors From Human Platelet Membranes", J. Med. Chem., 27, 918-921 (1984).

Di Chiara G., "Nucleus Accumbens Shell and Core Dopamine: Differential Role in Behavior and Addiction," Behavioural Brain Research, 137: 75-114 (2002).

Di Chiara et al., "Reward System and Addiction: What Dopamine Does and Doesn't Do," Current Opinion in Pharmacology 7:69-76 (2007).

Di Giovanni et al., "Serotonin/Dopamine Interaction-Focus on 5-HT2c Receptor, A Target of Psychotropic Drugs," Indian Journal of Experimental Biology, 40:1344-1352 (2002).

Di Matteo et al., "Role of 5-HT2c Receptors in the Control of Central Dopamine Function," Trends in Pharmacological Sciences 22(5):229-232 (2001).

Diagnostic and Statistical Manual of Mental Disorders, 4th edition, Text Revision, Washington, DC, American Psychiatric Association, 2000.

Dixit et al., "Genes Acting on Central Nervous System: Part XXIII: 2-Substituted 1,2,3,4,6,7,12, 12a-octahydropyrazino[2,i-b][3] benzazepines & 3-Substituted 1,2,3,4, 4a, 5, 6,11-Octahydropyrazin[i,2-b][2] benzazepines", CDRI Communication No. 1969,893-97 (1974).

Draper, et al., "Novel Stereoselective Syntheses of the Fused Benzazepine Dopamine Di Antagonist (6as, 13br)-ii-chloro-6, 6a,7,8,9, 13b-hexahydro-7-methyl-5h-benzo[d]naphth[2, lob]azepin-12-01 (sch 39166): 2. 1-Homophenylalanine-Based Syntheses", Organic Process Research & Development, 2(3):175-85 (1998).

Draper, et al., "Novel Stereoselective Syntheses of the Fused Benzazepine Dopamine Di Antagonist (6as, 13br)-ii-chloro-6, 6a,7,8,9, 13b-hexahydro-7-methyl-5h-benzo[d]naphth[2, lob]azepin-12-01 (sch 39166): 2. 1-Homophenylalanine-based Syntheses", Organic Process Research & Development, 2(3):186-93 (1998).

Flannery-Schroeder, "Reducing Anxiety to Prevent Depression," Am. J. Prev. Med. 31 (6S1): S136-S142 (2006).

Fuchs, et al., "Total Synthesis of (±)-Lennoxamine and (±)-Aphanorphine by Intramolecular Electrophilic Aromatic Substitution Reactions of 2-Amidoacroleins", Organic Letters, 3(24):3923-5 (2001).
Gallant et al., "U-22,394A: A Controlled Evaluation in Chronic Schizophrenic Patients," Current Therapy Research 9(11 ):579-81 (1967).
Gardent, et al., "Sur Quelques Proprietes De l'amino-2 Bromo-4 -H-benzazepine-3 et de ses derives", Bulletin de La Societe Chimique de France, 2:600-5 (1968) French Lang Only.
Gerace et al., "Predictors of Weight Increases Over 7 Years in Fire Fighters and Paramedics," Preventive Medicine 25:593-600 (1996).
Gerritz, et al., "Two General Routes to 1,4-Disubstituted-2,3,4,5-tetrahydro-1H-3-benzazepines", Organic Letters, 2(25):4099-102 (2000).
Gobert et al., "Serotonin2C Receptors Tonically Suppress the Activity of Mesocortical Dopaminergic and Adrenergic, but not Serotonergic, Pathways: A Combined Dialysis and Electrophysiological Analysis in the Rat," Synapse 36: 205-221 (2000).
Gombar, et al., "Pharmacokinetics of a Series of 6-Chloro-2,3,4,5-tetrahydro-3-substituted-1H-3-benzazepines in Rats", Drug Metabolism and Disposition, 16(3):367-72 (1988).
Greene et al., Protective Groups in Organic Syntheses, 2nd Ed., Wiley and Sons, NY (1991) (Index Only).
Griesser, "Polymorphism in the Pharmaceutical Industry," ed. Rolf Hilfiker, Wiley-VCH Verlag GmbH & Co.: pp. 211-233 (2006).
Halford et al., "Serotonergic Drugs: Effects on Appetite Expression and Use for the Treatment of Obesity," Drugs 67(1): 27-55 (2007).
Halford, et al., "o-Phenylenediacetimide and Other Compounds Related to 3,1H-Benzazepine", J. Org. Chem. 17:1646-52 (1952).
Hasan, et. al., "Syntheses of N-Chloroacyl-β -phenylethylamine Derivatives", Indian J. Chem., 9:1022-4 (1971).
Hashima. "Synthesis and Biological Activities of the Marine Bryozoan Alkaloids Convolutamines A, C and F, and Lutamides A and C", Bioorganic & Medicinal Chem, 2000, 8:1757-1766.
Helferich et al. "Uber Derivate Einger Chinolincarbonsauren," J. Fur Praktische Chemie, vol. 33, 1966, 39-48. German lang. only.
Hester et al., "Azepinoindoles. I. Hexahycloazepino[4,5-b]indoles," J. Med. Chem. 11(1): 101-106 (1968).
Heys, et al., "A New Entry Into C7-Oxygenated tetrahydro-1H-3-benzazepines: Efficient Labeling With Carbon-14 in The Benzo Ring", J. Org. Chem., 54(19):4702-6 (1989).
Higgins et al. Serotonin and Drug Reward: Focus on 5-$HT_{2C}$ Receptors. European J. Pharmacoloy 480:151-162 (2003).
Hitzig, P., "Combined Serotonin and Dopamine Indirect Agonists Correct Alcohol Craving and Alcohol-Associated Neuroses," Journal of Substance Abuse Treatment, 11 (5):489-90 (1994).
Im et al., "Positive Allosteric Modulator of the Human 5-HT2c Receptor," Molecular Pharmacology, 64: 78-84 (2003).
Jenck et al., "Antiaversive Effects of 5HT2c Receptor Agonists and Fluoxetine in a Model of Panic-Like Anxiety in Rats," European Neuropsychopharmacology 8: 161 (1998).
Jensen, "Potential Role of New Therapies in Modifying Cardiovascular Risk in Overweight Patients With Metabolic Risk Factors," Obesity 14 (Suppl. 3): 143S-149S (2006).
Kaiser, et al., "6-(Phenylthio)-Substituted 2,3,4,5-Tetrahydro-1H-3-benzazepines, A Novel Class of Dopamine Receptor Agonists and Neuroleptics", J. Med. Chem., 23(9):975:6 (1980).
Karasu et al., (2000) Practice Guideline for the Treatment of Patients With Major Depressive Disorder.
Klohr, et al., "An Intramolecular Photocyclization to Form the Azepino[3,4,5-Cd]Indole System", Synthetic Communications 18(7):671-4 (1988).
Koplan et al., "Preventing Childhood Obesity: Health in the Balance, Executive summary," (2005).
Krull et al. "Synthesis and Structure/NMDA Receptor Affinity Relationships of 1-Substituted Tetrahydro-3-benzazepines", Bioorganic & Medicinal Chem. 12(6), 1439-1451 (2004).
Küenburg, et al., "Development of a Pilot Scale Process for the Anti-Alzheimer Drug (−)-Galanthamine Using Large-Scale Phenolic Oxidative Coupling and Crystallisation-Induced Chiral Conversion", Organic Process Research & Development, 3(6):425-31 (1999).

Ladd, et al., "Synthesis of a Dopaminergic Binding of 2-Aryldopamine Analogues: Phenethylamines, 3-Benzazepines, and 9-(Aminomethyl) Fluorenes", J. Med. Chem. 29(10):1904-12(1986).
Lam RW, Levitt AJ (1999) (eds) Canadian Consensus Guidelines for the Treatment of Seasonal Affective Disorder, Clinical & Academic Publishing, Vancouver, BC, Canada.
Lennon, et al., "Azabenzocycloheptenones. Part XVII. Amines and Amino-Ketones of the Tetrahydro-3-Benzazepin-1-one Series", J.C.S. Perkin I, 7:622-6 (1975).
Lin, et al., "Benzindene Prostaglandins. Synthesis of Optically Pure 15-Deoxy-U-68,215 and Its Enantiomer Via a Modified Intramolecular Wadsworth-Emmons-Wittig Reaction", J. Org. Chem., 52(25):5594-601 (1987).
MacDonald, et al., "Design and Synthesis of Trans-3-(2-(4-<<3-(3-(5-Methyl-I ,2,4-oxadiazolyl>>-phenyl)carboxamido)cyclohexypethyl)ethyl)-7-methylsulfonyl-2,3,4,5-tetrahydro-1H-3-benzazepine (SB-414796): A Potent and Selective Dopamine D3 Receptor Antagonist", J. Med. Chem., 46(23):4952-64 (2003).
Moline et al., "Postpartum Depression: A Guide for Patients and Families," Expert Consensus Guidelines Series—Treatment of Depression in Woman Mar. 2001: 113(2001).
Muller et al., "Intracellular 5-HT2c-Receptor Dephosphorylation: A New Target for Treating Drug Addiction," Trends in Pharmacological Sciences, 27(9):455-58 (2006).
Nagase et al., "An Anhydrous Polymorphic Form of Trehalose," Carbohydrate 337(2),167-173 (2002).
Nagle, et al. "Efficient Synthesis of β-Amino bromides", Tetrahedron Letters, 41 :30 11-4 (2000).
Nair, et al., "Preparation of 2,3,4,5-Tetrahydro-3,1H-benzazepine-2-one", Indian J. Chem., 5:169-70 (1967).
Navarro-Vasquez et al., "A Study of Aryl Radical Cyclization in Enaminone Esters," J. Org. Chem. 67:3213-20 (2002).
Neumeyer, et al., "Development of a High Affinity and Stereoselective Photoaffinity Label for the D-I Dopamine Receptor: Synthesis and Resolution Of 7-[$^{125}$ 1]Iodo-8-hydroxy-3-methyl-l-(4'-azidophenyl)-2,3,4,5-tetrahydro-1H-3-benzazepine", J. Med. Chem., 33(2):521-6 (1990).
Niendam et al., "Neurocognitive Performance and Functional Disability in the Psychosis Prodrome," Schizophrenia Research 84: 100-111 (2006).
Ohnmacht, et al. Naphtho[2,1-b][1,5]- and [1,2-f][1,4]oxazocines as Selective NK1 Antagonists. Bioorganic & Medicinal Chem. 2004, vol. 12, No. 10, pp. 2653-266.
Okuno, et al., "Photocyclization of N-Chloroacetyl-2,5-Dimethoxyphenethylamine Synthesis of Pyrroloindoles", Chem. Pharm. Bull., 23(11):2584-90 (1975).
Orito et al., "Benzolactams-1: Alkylation of 1,2,4,5-Tetrahydro-3-Methyl-3H-3-Benzazepin-2-One With Sodium Hydride and Alkyl Halide," Tetrahedron 36:1017-1021 (1980).
Orito, et al., "Synthetic Studies of Heterocyclic Compounds 1: Alkylation and Acylation of 1, 2, 4,5-Tetrahydro-3-Methyl-3H-3-Benzepin-2-one", Bulletin of the Faculty of Engineering, Hokkaido University (Hokkaido Kogakubu Kenkyu Hokuko), 96(54):41-4 (1979).
Orito, et al., "Total Synthesis of Pseudo Type of Protopine Alkaloids", Heterocycles, 14(1): 11-4 (1980).
Pauvert, et al., "Silver Ntrate-Promoted Ring Enlargement of 1-Tribromomethyl-1,2-Dihydro-and 1-Tribromethyl-1,2, 3,4-Tetrahydro-Isoquinoline Derivatives: Application to the Synthesis of the Anti-Anginal Zatebradine", Tetrahedron Letters, 44:4203-6 (2003).
Pawan et al., "Preliminary Study on the Effects of Fenfluramine Derivative, 'S992' In Man," British Journal of Pharmacology, 41(2): 416P-417P (1971).
Pecherer, et al., "A Novel Synthesis of Aromatic Methoxy and Methylenedioxy Substituted 2,3,4,5-Tetrahydro-1-H3-benzazepines", J. Het. Chem., 9:609-16 (1972).
Pecherer, et al., "The Synthesis of Some 7-and 7,8-Substituted 2,3,4,5-Tetrahydro-1H-3-benzazepines", J. Het. Chem., 8:779-83 (1971).

Perry, et al., "Prospective Study of Risk Factors for Development of Non-Insulin Dependent Diabetes in Middle Aged British Men", BMJ, 310:560-4 (1995).

Pfeiffer, et al., "Dopaminergic Activity of Substituted 6-Chloro-l-phenyl-2,3,4,5-tetrahydro-1h-3-benzazepines", J. Med. Chem., 25(4):352-8 (1982).

Porras et al., "5-HT2A and 5-HT2C/2B Receptor Subtypes Modulate Dopamine Release Induced In Vivo by Amphetamine and Morphine in Both the Rat Nucleus Accumbens and Striatum," Neuropsychopharmacology 26: 311-324 (2002).

Prous Science Integrity entry 156186, 2005.

Prous Science Integrity entry 354056, 2006.

Rothman R.B., "Treatment of Alcohol and Cocaine Addiction by the Combination of Pemoline and Fenfluramine: A Preliminary Case Series," Journal of Substance Abuse Treatment, 12(6):449-53 (1995).

Schaffner et al., "Preventing Severe Mental Illnesses—New Prospects and Ethical Challenges," Schizophrenia Research 51:3-15 (2001).

Schlademan, et al., "Synthesis of 1-Oxo-and 1-Hydroxy-azabenzocycloalkanes", J.C.S. Perkin I, 2:213-5 (1972).

Smith et al., "Discovery and SAR of New Benzazepines as Potent and Selective 5-HT2c Receptor Agonists for the Treatment of Obesity," Bioorganic & Medicinal Chemistry Letters 15(5):1467-1470 (2005).

Tietze, et al., "Efficient Synthesis of 2,3,4,5-tetrahydro-1H-3-benzazepines by Intramolecular Heck Reaction", Synthesis, 9:876-80 (1993).

Tsuang et al., "Towards the Prevention of Schizophrenia," B245 Biol. Psychiatry 48:349-356 (2000).

U.S. Appl. No. 11/599,050. Notice of Allowance dated Feb. 28, 2011.

U.S. Appl. No. 11/793,473. Non-Final Office Action dated May 10, 2011.

U.S. Appl. No. 11/793,473. Notice of allowance dated Jan. 5, 2012.

U.S. Appl. No. 11/793,941 Final Office Action dated Aug. 10, 2011.

U.S. Appl. No. 11/793,941 Non-Final Office Action dated Mar. 4, 2011.

U.S. Appl. No. 11/793,941. Notice of Allowance dated Dec. 2, 2011.

U.S. Appl. No. 12/517,625. Non-Final Office Action dated Jan. 27, 2012.

U.S. Appl. No. 12/225,966. Non-Final Office Action dated Sep. 2, 2011.

U.S. Appl. No. 12/225,966. Notice of Allowance mailed Dec. 30 2011.

U.S. Appl. No. 12/729,026. Non-Final Office Action dated Jan. 26, 2012.

U.S. Appl. No. 13/118,126. Non-Final Office Action dated Mar. 30, 2012.

U.S. Appl. No. 10/560,953. Final Office Action dated Jan. 27, 2011.

U.S. Appl. No. 10/560,953. Non-Final Office Action dated Jan. 11, 2012.

U.S. Appl. No. 10/560,953. Non-final Office Action dated Aug. 17, 2010.

U.S. Appl. No. 11/599,050. Final Office Action dated Aug. 20, 2010.

U.S. Appl. No. 11/793,941. Non-final Office Action (Restriction Requirement) dated Sep. 17, 2010.

Van Oekelen et al., "5-HT2A and 5-HT2c Receptors and Their Atypical Regulation Properties," Life Sciences, vol. 72:pp. 2429-2449 (2003).

Vanderlaan, et al., "Synthesis and Oxidative Coupling of (±)-3-Oxoreticuline", J. Org. Chem., 50(6):743-7 (1985).

Weinstock, et al., "Separation of Potent Central and Renal Dopamine Agonist Activity in Substituted 6-Chloro-2,3,4,5-tetrahydro-7,8-dihydroxy-l-phenyl-IH-3-benzazepines", J. Med. Chem., 23(9):973-5 (1980).

Wilk, Exchange Type Reactions Between Oxiranes or Thiiranes and 2-Hydroxyalkyl or 2-Thioalkyl Amines and Sulfides. Polish J. Chem (1988).

Williams, Chemistry Demystified 123 (2003).

Wise, "Addiction Becomes a Brain Disease," Neuron, 26: 27-33 (2000).

Wisner et al., "Postpartum Depression," N. Eng. J. Med., 347(3):194-199 (2002).

Woods et al., "Annual Report: Evaluation of New Compounds for Opioid Activity," National Institute on Drug Abuse, Proceedings of the 41st Annual Scientific Meeting (1979) pp. 356-401.

Wu, et al., "Amino Diol Based Asymmetric Syntheses of a Fused Benzazepine As a Selective D1 Dopamine Receptor", Organic Process Research & Development, 1(5):359-64 (1997).

Yasuda, et al., "A Novel and Stereoselective Synthesis of (±)-Cephalotaxine and Its Analogue", Tetrahedron Letters, 27(18):2023-6 (1986).

Yonemitsu, et al., "Photocyclization of Pharmacodynamic Amines. IV. Novel Heterocycles From N-Chloroacetyl-3,4-Dimethoxyphenethylamine", Journal of the American Chemical Society, 92(19):5686-90 (1970).

Yonemitsu, et al., "Photocyclization of Pharmodynamic Amines. II. X-Ray Analysis of Noncentrosymmetric Tetracyclic Indole", Journal of the American Chemical Society, 90(23):6522-3 (1968).

Yonemitsu, et al., "Photocyclizations of Tyrosines, Tyramines, Catecholamines, and Normescaline", Journal of the American Chemical Society, 90(3):776-84 (1968).

Yonemitsu, et al., "Photolysis of N-Chloroacetyl-O-Methyl-L-Tyrosine to an Azaazulene", Journal of the American Chemical Society, 89(4):1039-40 (1967).

Yoshinaga et al., "Prevention of Mildly Overweight Children from Development of More Overweight Condition," Prevention Medicine 38:172-174 (2004).

Zhang, et al. "Convolutamines A-E, Novel B-Phenylethylamine Alkaloids From Marine Bryozoan Amathia Convolute", Chem. Lett. 1994, vol. 12, pp. 2271-2274.

PROCESSES FOR PREPARING (R)-8-CHLORO-1-METHYL-2,3,4,5-TETRAHYDRO-1H-3-BENZAZEPINE AND INTERMEDIATES THEREOF

CROSS REFERENCE TO RELATED APPLICATIONS

This application is a 35 U.S.C. §371 National Stage Application of International Appl. No. PCT/US2007/024900, filed Dec. 4, 2007, which claims the benefit of priority of U.S. Provisional Appl. No. 60/873,036, filed Dec. 5, 2006.

FIELD OF THE INVENTION

The present invention generally relates to processes and intermediates for the preparation of (R)-8-chloro-1-methyl-2,3,4,5-tetrahydro-1H-3-benzazepine, and solid forms thereof, which are serotonin-2C (5-HT$_{2C}$) receptor agonists useful in the treatment of, for example, obesity.

BACKGROUND OF THE INVENTION

Serotonin (5-HT) neurotransmission plays an important role in numerous physiological processes both in health and in psychiatric disorders. For example, 5-HT has been implicated in the regulation of feeding behavior. 5-HT is believed to work by inducing a feeling of fullness or satiety so eating stops earlier and fewer calories are consumed. It has been shown that a stimulatory action of 5-HT on the 5-HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-HT$_{2C}$ receptor agonist can be a more effective and safe anti-obesity agent. Also, 5-HT$_{2C}$ knockout mice are overweight with cognitive impairment and susceptibility to seizure. Thus, the 5-HT$_{2C}$ receptor is recognized as a well-accepted receptor target for the treatment of obesity, psychiatric, and other disorders.

Lorcaserin hydrochloride (8-chloro-1-methyl-2,3,4,5-tetrahydro-1H-3-benzazepine hydrochloride) is an agonist of the 5-HT$_{2C}$ receptor and shows effectiveness at reducing obesity in animal models and humans. Patients enrolled in a 12-week Phase IIb clinical trial achieved a highly statistically significant mean weight loss of 4.0, 5.7, and 7.9 pounds at daily doses of 10 mg, 15 mg, and 20 mg (10 mg dosed twice daily), respectively, compared to 0.7 pounds for the placebo group. The proportion of patients completing the treatment period who achieved a 5% or greater weight loss from baseline were 13%, 20%, and 31% at daily doses of 10 mg, 15 mg, and 20 mg, respectively, compared with 2% in the placebo group. This data, showing statistically significant, progressive, and dose-dependant weight loss, coupled with the drug's favorable tolerability profile make locaserin hydrochloride an attractive new therapy for obesity, and accordingly, Phase III clinical trials are underway. Various synthetic routes to locaserin hydrochloride, its related salts, enantiomers, crystalline forms, and intermediates, have been reported in WO 2005/019179, WO 2006/069363, and U.S. Pat. No. 6,953,787.

In view of the growing demand for compounds for the treatment of disorders related to the 5-HT$_{2C}$ receptor, new and more efficient routes to 3-benzazepines, including locaserin hydrochloride, are needed. The processes and compounds described herein help meet these and other needs.

SUMMARY OF THE INVENTION

The present invention provides intermediates, processes of preparing the same, and compositions containing the same, which are useful in the preparation of (R)-8-chloro-1-methyl-2,3,4,5-tetrahydro-1H-3-benzazepine, and solid forms thereof, for the treatment or prophylaxis of 5-HT$_{2C}$ associated disorders such as obesity and central nervous system diseases.

The present invention provides processes for preparing an amide compound of Formula 1-3 and optionally a dihydrooxazole compound of Formula 1-4, or salt thereof:

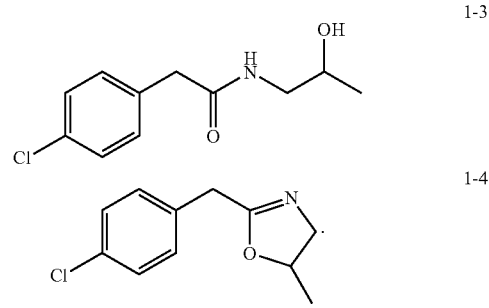

The present invention further provides processes for preparing an amino alcohol compound of Formula 2-1, or salt thereof:

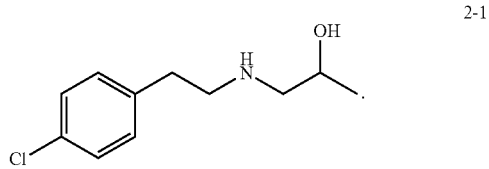

The present invention further provides the amide compound of Formula 1-3, the dihydrooxazole compound of Formula 1-4, mixtures thereof, and compositions containing the same.

The present invention further provides processes for preparing a compound of Formula 3-5:

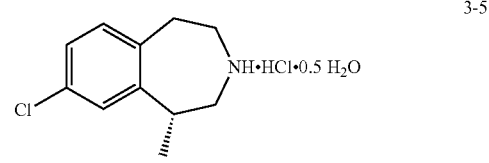

utilizing the amide compound of Formula 1-3, the dihydrooxazole compound of Formula 1-4, or mixtures thereof.

DETAILED DESCRIPTION

The processes and intermediates of the present invention are useful in the preparation of therapeutic agents for the treatment or prophylaxis of 5-HT$_{2C}$ associated disorders such as obesity and central nervous system diseases. Example processes and intermediates of the present invention are provided below in Schemes 1, 2 and 3.

Scheme 1

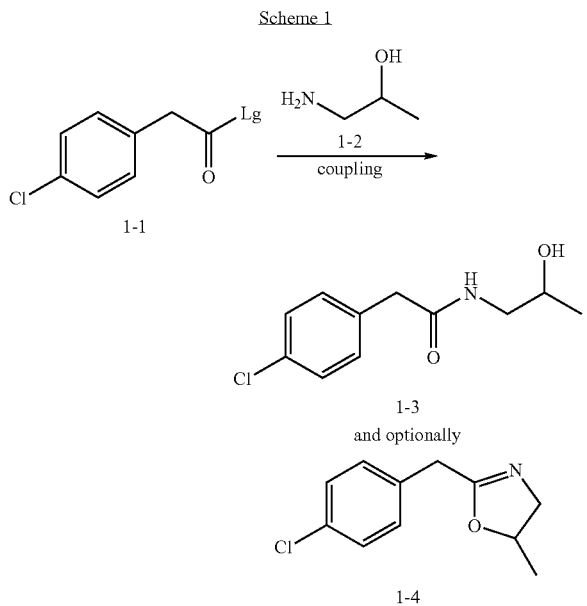

Scheme 1 depicts a general route to intermediates 1-3 and optionally 1-4. Accordingly, the present invention provides amide-forming processes for preparing amide compounds of Formula 1-3:

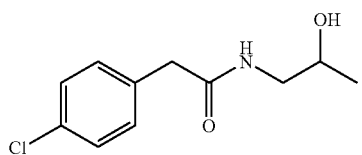

comprising reacting a phenylacetic acid derivative compound of Formula 1-1:

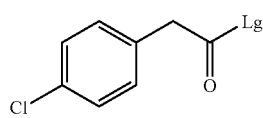

or salt thereof, wherein Lg is a leaving group, with an amine compound of Formula 1-2:

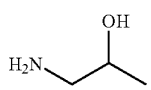

or salt thereof, in the presence of a coupling reagent to afford the amide compound of Formula 1-3.

In some embodiments, Lg is OH, halo, or other leaving group. As used herein, the term "leaving group" refers to a moiety that can be displaced by another moiety, such as by nucleophilic attack, during a chemical reaction. Leaving groups are well known in the art and include, for example, halo, hydroxy, —$OR^a$, and —$OSi(R^b)_3$ wherein $R^a$ can be $C_{1-8}$ alkyl, $C_{3-7}$ cycloalkyl, aryl, heteroaryl, or heterocycloalkyl, and $R^b$ can be $C_1$-$C_8$ alkyl. In some embodiments, Lg is OH. In further embodiments, Lg is halo such as fluoro, chloro, bromo, or iodo. In yet further embodiments, Lg is chloro.

The term "coupling reagent," as used herein, is meant to refer to a reagent or combination of reagents that facilitates formation of an amide bond between the phenylacetic acid derivative compound of Formula 1-1 and the amine compound of Formula 1-2. Suitable coupling reagents include, for example, boron-containing acids, carbodiimides, and ketals. Further examples of coupling reagents include bases.

Suitable boron-containing acids include, for example, boric acid ($B(OH)_3$), boronic acids (e.g., boric acid wherein at least one OH group is replaced with an organic moiety), or combinations thereof. In some embodiments, the boronic acid is an optionally substituted arylboronic acid such as phenylboronic acid or 2,5,6-trifluorophenylboronic acid. In some embodiments, the coupling reagent contains phenylboronic acid, boric acid, or mixture thereof. In yet further embodiments, the coupling reagent contains a halo-substituted arylboronic acid such as 2,5,6-trifluorophenylboronic acid. In some embodiments when the coupling reagent contains at least one boron-containing acid, Lg is OH.

Suitable carbodiimides include any reagent containing a carbodiimide (N=C=N) functionality that can serve as a carboxyl activating group to facilitate amide bond formation. An example carbodiimide is 1-ethyl-3-(3-dimethylaminopropyl)-carbodiimide hydrochloride (EDC). Other suitable carbodiimides include dicyclohexylcarbodiimide (DCC), diisopropylcarbodiimide (DIC), N-cyclohexyl-N'-(□-N-methylmorpholino)ethylcarbodiimide (CMC), and the like. In some embodiments when the coupling reagent contains at least one carbodiimide, Lg is OH.

Suitable ketals can have the formula:

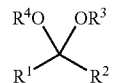

wherein $R^1$, $R^2$, $R^3$, and $R^4$ are $C_{1-6}$ alkyl. In some embodiments, $R^1$, $R^2$, $R^3$, and $R^4$ are independently selected from methyl and ethyl. In yet further embodiments, the ketal comprises 2,2-dimethoxypropane. In some embodiments when the coupling reagent contains at least one ketal, Lg is OH.

Suitable bases for use as a coupling reagent include any base effective for facilitating formation of an amide bond and which do not substantially interfere with the amide-forming reaction. Example bases include tertiary amines such as tri($C_{1-6}$)alkylamines. In some embodiments, the base is triethylamine. In some embodiments when the coupling reagent contains a base, Lg is halo.

The above process for preparing amides of Formula 1-3 can further yield a dihydrooxazole compound of Formula 1-4:

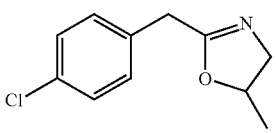

or salt thereof. The dihydrooxazole compound of Formula 1-4 is related to the amide of Formula 1-3 by the loss of one water molecule. Accordingly, the dihydrooxazole compound of Formula 1-4 is typically formed under dehydrating reaction conditions, such as when the coupling reagent further acts as a dehydrating agent. Example coupling reagents capable of this dual coupling/dehydrating activity include, for example, carbodiimides and ketals. The dihydrooxazole compound of Formula 1-4 can be produced in variable amounts, but is usually observed as a minor product relative to the amide of Formula 1-3.

The amide-forming process as described above can be carried out where the coupling reagent is provided in molar excess relative to either the phenylacetic acid derivative compound of Formula 1-1 or the amino compound of Formula 1-2. In some embodiments, the molar ratio of the phenylacetic acid derivative compound of Formula 1-1 to the coupling reagent is about 1:1 to about 20:1, about 1:1 to about 10:1, or about 1:1 to about 5:1.

The above amide-forming process can further be optionally carried out in the presence of a solvent such as an aromatic solvent or an alcohol solvent. Typical aromatic solvents include, for example, benzene, chlorobenzene, 1,2-dichlorobenzene, toluene, o-xylene, p-xylene, m-xylene, xylenes, mixtures thereof and the like. Typical alcohol solvents include, for example, methanol, ethanol, n-propanol, isopropanol, n-butanol, isobutanol, t-butanol, glycols, glycerols, mixtures thereof and the like. In some embodiments, the solvent includes toluene. In further embodiments, the solvent includes methanol, ethanol, or isopropanol.

The above amide-forming process can further be optionally carried out in the presence of an acid catalyst. In some embodiments, the acid catalyst comprises a sulfonic acid such as an optionally substituted arylsulfonic acid (e.g., p-toluenesulfonic acid). Other suitable acid catalysts include sulfuric acid, benzenesulfonic acid, trifluoromethansulfonic acid, hydrochloric acid, mixtures thereof and the like. In some embodiments, the acid catalyst is present when the coupling reagent includes a ketal.

The above amide-forming process can be carried out at about room temperature or at an elevated temperature. In some embodiments, the elevated temperature is about 80° C. to about 140° C. In further embodiments, the temperature is room temperature when the coupling reagent includes a carbodiimide.

In some embodiments, the present invention provides processes for preparing an amide compound of Formula 1-3 comprising reacting, in a solvent comprising toluene and at elevated temperature, a phenylacetic acid derivative compound of Formula 1-1, or salt thereof, with an amine compound of Formula 1-2, or salt thereof, in the presence of at least one boron-containing acid. In further embodiments, the reacting is carried out in the presence of phenylboronic acid, boric acid, or mixture thereof. In yet further embodiments, the reacting is carried out in the presence of 2,5,6-trifluorophenylboronic acid.

In some embodiments, the present invention provides processes for preparing an amide compound of Formula 1-3 and optionally a dihydrooxazole compound of Formula 1-4, or salt thereof, comprising reacting, in a solvent comprising isopropyl alcohol and at about room temperature, a phenylacetic acid derivative compound of Formula 1-1, or salt thereof, with an amine compound of Formula 1-2, or salt thereof, in the presence of 1-ethyl-3-(3-dimethylaminopropyl)-carbodiimide hydrochloride (EDC).

In some embodiments, the present invention further provides processes for preparing an amide compound of Formula 1-3 and optionally a dihydrooxazole compound of Formula 1-4, or salt thereof, comprising reacting, in an alcohol solvent and optionally in the presence of an acid catalyst, a phenylacetic acid derivative compound of Formula 1-1, or salt thereof, with an amine compound of Formula 1-2, or salt thereof, in the presence of 2,2-dimethoxypropane. In some embodiments, the above process further comprises combining the 2,2-dimethoxypropane with the phenylacetic acid derivative compound of Formula 1-1 prior to reacting with the amine compound of Formula 1-2, or salt thereof. In some embodiments, the prior combining affords 2-(4-chlorophenyl)acetic acid methyl ester which is then subject to reaction with the amine compound of Formula 1-2. In some embodiments, conversion to 2-(4-chlorophenyl)acetic acid methyl ester is about 90% or greater. The prior combining of the phenylacetic acid derivative compound of Formula 1-1 with 2,2-dimethoxypropane can be carried out at elevated temperature such as about 60° C. to about 120° C.

The present invention further provides an amide compound of Formula 1-3 or a dihydrooxazole compound of Formula 1-4, or salt thereof. Further provided are compositions containing an amide compound of Formula 1-3 or a dihydrooxazole compound of Formula 1-4, or salt thereof. In some embodiments, the compositions contain a mixture of an amide compound of Formula 1-3 and a dihydrooxazole compound of Formula 1-4, or salt thereof.

Scheme 2 provides a general route to amino alcohols of Formula 2-1 or salts thereof.

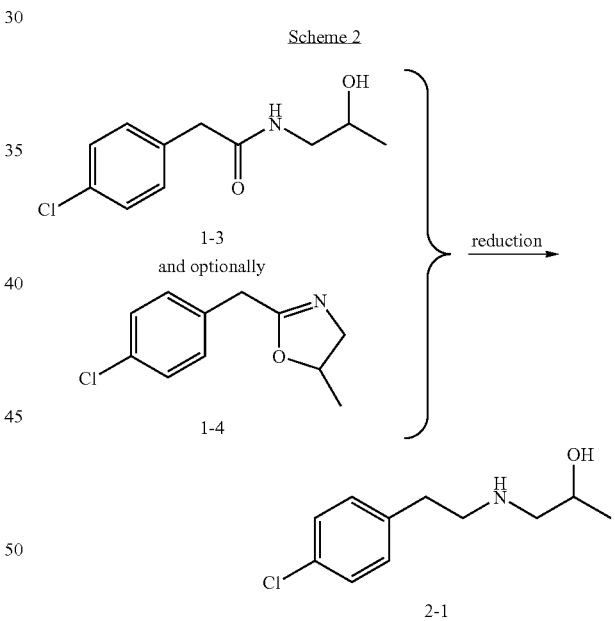

Accordingly, the present invention provides amine-forming processes for preparing an amino alcohol compound of Formula 2-1:

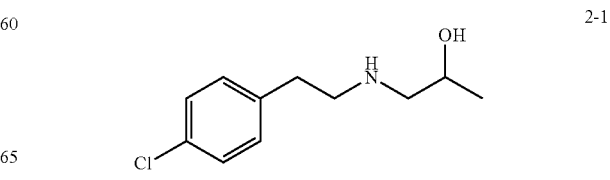

or salt thereof, comprising reacting an amide compound of Formula 1-3 and optionally reacting a dihydrooxazole compound of Formula 1-4, or salt thereof, with a reducing agent.

Suitable reducing agents include any reagent that can effectively reduce an amide to an amine such as, for example, boranes (e.g., BH$_3$, BH$_3$ adducts, diborane, higher boranes, and the like), organoboranes (e.g., alkylboranes, dialkylboranes, etc.), alkali metal trialkylboron hydrides, alkali metal aluminum hydrides, alkali metal borohydrides, alkali metal trialkoxyaluminum hydrides, dialkylaluminum hydrides, or H$_2$ optionally in the presence of a catalyst. In some embodiments, the reducing agent comprises BH$_3$. In further embodiments, the BH$_3$ is generated in situ. In yet further embodiments, the reducing agent comprises a borane complex such as a borane tetrahydrofuran complex or a borane methylsulfide complex.

In some embodiments, the reducing agent is provided in molar excess relative to the amide compound of Formula 1-3. For example, the molar ratio of reducing agent to amide compound of Formula 1-3 can be about 1:1 to about 10:1, about 1:1 to about 5:1, or about 3.5:1.

In yet further embodiments, the reducing agent comprises NaBH$_4$ in the presence of iodine. For example, the molar ratio of NaBH$_4$ to iodine to said amide compound of Formula 1-3 can be about 10:1:1, about 5:1:1, or about 2.5:1:1.

The above amine-forming process can be carried out at elevated temperature such as at about 30° C. to about 80° C., about 40° C. to about 70° C., or about 50° C. to about 60° C.

The above amine-forming process can result in a conversion of the amide compound of Formula 1-3 to the amino alcohol compound of Formula 2-1, or salt thereof, of about 90% or greater, about 95% or greater, or about 97% or greater.

The amide compound of Formula 1-3 employed in the amine-forming process above can be prepared according to any appropriate process, including any of those described herein.

The dihydrooxazole compound of Formula 1-4 optionally employed in the amine-forming process above can be prepared according to any appropriate process, including any of those described herein.

Scheme 3 provides a general route to 3-benzazepine compounds of Formulas 3-2, 3-3, 3-4, and 3-5 starting from amino alcohol 2-1 or salt thereof.

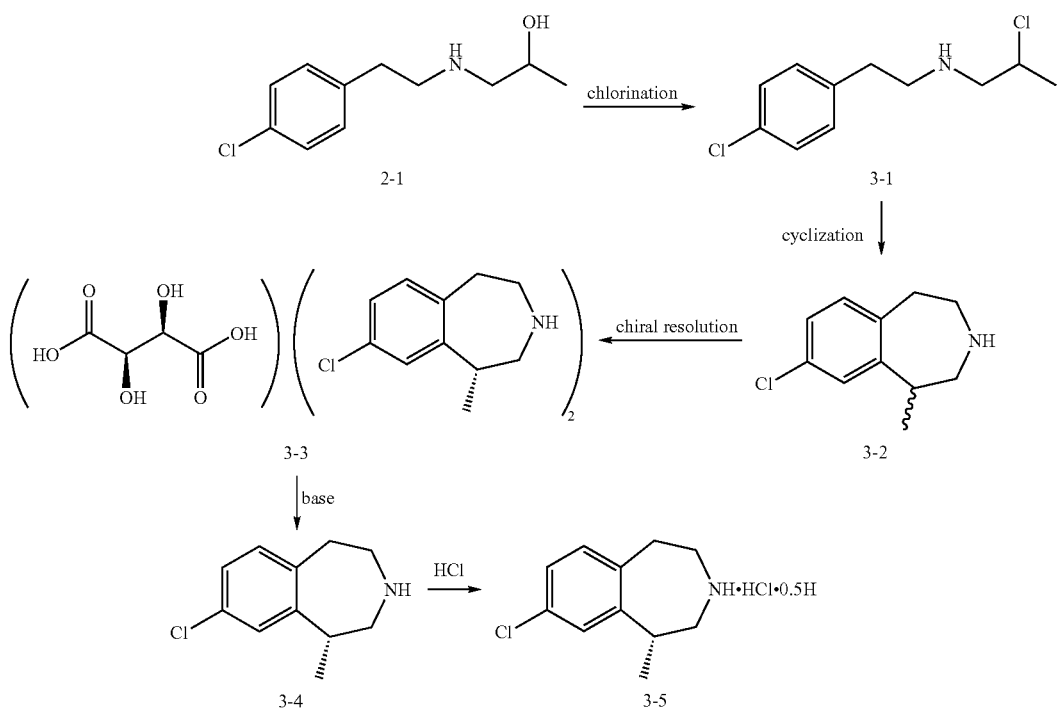

The present invention provides processes for preparing a compound of Formula 3-5:

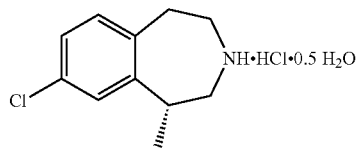

comprising:

a) reacting a phenylacetic acid derivative compound of Formula 1-1, or salt thereof, with an amine compound of Formula 1-2, or salt thereof, in the presence of a coupling reagent to afford an amide compound of Formula 1-3 and optionally a dihydrooxazole compound of Formula 1-4, or salt thereof;

b) reacting the amide compound of Formula 1-3 and optionally the dihydrooxazole compound of Formula 1-4, or salt thereof, with a reducing agent to afford an amino alcohol compound of Formula 2-1, or salt thereof;

c) reacting the amino alcohol compound of Formula 2-1, or salt thereof, with a chlorinating reagent to afford a dichloro compound of Formula 3-1:

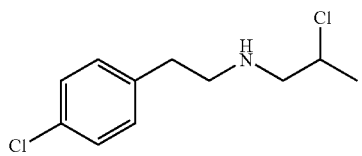

3-1 or salt thereof;

d) reacting the dichloro compound of Formula 3-1 with a cyclizing reagent to afford a 3-benzazepine compound of Formula 3-2:

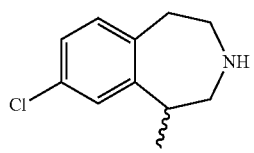

3-2 e) contacting the 3-benzazepine compound of Formula 3-2 with L-(+)-tartaric acid to afford a tartrate salt of Formula 3-3:

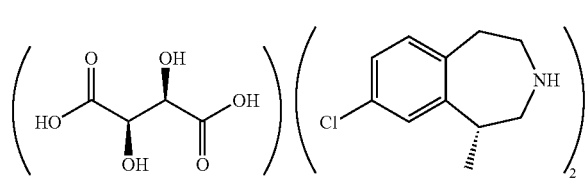

3-3 f) reacting the tartrate salt of Formula 3-3 with a base to afford the optically active compound of Formula 3-4:

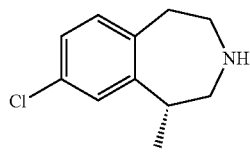

3-4 and g) reacting the optically active compound of Formula 3-4 with HCl to afford the compound of Formula 3-5.

The reacting of steps a) and b) can be carried out according to any of the procedures set out herein.

As used herein, the term "chlorinating reagent" refers to any chemical reagent that can be used to replace a hydroxyl group with a chloro group. Example chlorinating reagents include thionyl chloride ($SOCl_2$), $SO_2Cl_2$, $PCl_3$, $PCl_5$, $POCl_3$, mixtures thereof and the like. In some embodiments, the chlorinating reagent is thionyl chloride. Chlorinating reagents can be provided in molar excess relative to the amino alcohol compound of Formula 2-1. In some embodiments, the molar ratio of chlorinating reagent to amino alcohol compound of Formula 2-1 is about 20:1 to about 2:1, about 10:1 to about 2:1, or about 5:1 to about 2:1.

The chlorinating reaction of step c) can be carried out in the presence of solvent such as an aromatic solvent (e.g., any of those disclosed herein) or an amide solvent. In some embodiments, the aromatic solvent contains toluene. In some embodiments, the amide solvent contains N,N-dimethylformamide (DMF) or N,N-dimethylacetamide (DMA). In some embodiments, the solvent contains a mixture of toluene and DMA. In some embodiments, the reaction of step c) is carried out in substantially no solvent.

The chlorinating reaction of step c) can further be conducted at elevated temperature. Suitable temperatures include about 40° C. to about 75° C., about 50° C. to about 70° C., or about 55° C. to about 65° C.

As used herein, the term "cyclizing reagent" refers to any chemical reagent that can be used in a reaction to cyclize a linear or branched molecule or portion of a molecule. In some embodiments according to the present invention, cyclization of a linear or branched moiety attached to an aryl compound can be carried out using, for example, a Lewis acid. As is known in the art, a Lewis acid includes a molecule that can accept a lone pair of electrons. Example Lewis acids include hydrogen ion (a proton), boron derivatives such as $BH_3$ and $BF_3$, and aluminum derivatives such as $AlCl_3$. Some example Lewis acids include $C_{1-8}$ alkylaluminum halide (e.g., methylaluminum chloride, ethylaluminum chloride, etc.), a $C_{2-16}$ dialkylaluminum halide (e.g., dimethylaluminum chloride, diethylaluminum chloride, etc.), and $C_{3-24}$ trialkylaluminum. In some embodiments, the cyclizing reagent includes aluminum chloride.

The cyclizing reagent can be provided in molar excess relative to the amount of dichloro compound of Formula 3-1 For example, the molar ratio of cyclizing reagent to dichloro compound of Formula can be about 5:1 to about 1:1, about 2.5:1 to about 1:1, or about 1.5:1 to about 1:1.

The cyclizing reaction of step d) can be conducted at elevated temperatures. Suitable temperatures include, for example, about 100° C. to about 150° C., about 110° C. to about 140° C., or about 125° C. to about 130° C.

The cyclizing reaction of step d) can further be conducted in the presence of solvent such as an aromatic solvent. In some embodiments, the aromatic solvent includes 1,2-dichlorobenzene.

The contacting of step e), forming the tartrate salt, can be carried out in the presence of solvent. Suitable solvents support dissolution of both L-(+)-tartaric acid and the 3-benzazepine compound of Formula 3-2. Some example solvents include alcohols (e.g., methanol, ethanol, isopropanol, t-butanol, 1-butanol and the like), isopropylacetate, tetrahydrofuran, acetone, methyl isobutyl ketone, water, and mixtures thereof. In some embodiments, the solvent contains a mixture of water and acetone. A suitable molar ratio of 3-benzazepine: acetone:L-(+)-tartaric acid:water is about 1:9.6:0.25:3.6.

The contacting of step e) can further be carried out at elevated temperature. Suitable temperatures include, for example, about 40° C. to about 60° C., about 45° C. to about 55° C., or about 47° C. to about 52° C.

The base of step f) can be any suitable base that will free the optically active compound 3-4 from the tartrate salt. Example bases include lithium hydroxide, sodium hydroxide, potassium hydroxide, lithium carbonate, sodium carbonate, and potassium carbonate. In some embodiments, the base is a carbonate such as potassium carbonate. The reacting of the base with the tartrate salt 3-3 can be carried out in a two phase system containing, for example water and an organic solvent such as ethyl acetate. Base can be provided in molar excess such as a molar ratio of base to tartrate salt of Formula 3-3 of about 10:1 to about 2:1, about 5:1 to about 2:1, or about 3:1 to about 2:1.

The reacting of step g) can be carried out in the presence of water and organic solvent such as ethyl acetate. HCl can be provided in solution or in gaseous form. In some embodiments, the molar ratio of HCl to optically active compound of Formula 3-4 is about 1:1 to about 10:1, about 1:1 to about 5:1, or about 1:1 to about 2:1. Suitable temperatures for the reacting of step g) include, for example, about −5° C. to about 15° C., about 0° C. to about 10° C., or 0° C. to about 5° C.

As used herein, the term "reacting" is used as known in the art and generally refers to the bringing together of chemical reagents in such a manner so as to allow their interaction at the molecular level to achieve a chemical or physical transformation.

As used herein, the term "contacting" refers to the bringing together of substances so that they can interact at the molecular level.

The reacting and contacting steps of the processes described herein can be conducted for a time and under conditions suitable for preparing the identified product.

As used herein, "or salt thereof" refers to derivatives of the disclosed compounds wherein the parent compound is modified by converting an existing acid or base moiety to its salt form. Examples of suitable salts include, but are not limited to, mineral or organic acid salts of basic residues such as amines; alkali or organic salts of acidic residues such as carboxylic acids; and the like. The acceptable salts include the conventional non-toxic salts of the parent compound formed, for example, from non-toxic inorganic or organic acids. The salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are suitable.

As used herein, the term "composition" refers to a mixture of at least two different substances. In some embodiments, a composition can contain an intermediate described herein together with one or more other substances such as solvents, reagents, other intermediates, impurities, reaction byproducts, and the like.

As used herein, the term "substituted" refers to the replacement of a hydrogen moiety with a non-hydrogen moiety. A substituted group or molecule can be substituted at any open position up to the maximum valency. In some embodiments, a substituted group or molecule is substituted with 0, 1, 2, or 3 substituents. Example substituents include halo, $C_{1-6}$ alkyl, $C_{2-6}$ alkenyl, $C_{2-6}$ alkynyl, CN, OH, $C_{1-6}$ alkoxy, carboxy, carboxy alkyl ester, aminocarbonyl, $NO_2$, amino, $C_{1-6}$ alkylamino, $C_{2-12}$ dialkylamino, aryl, heteroaryl, cycloalkyl, or heterocycloalkyl.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more carbon-carbon double bonds. Example alkenyl groups include ethenyl, propenyl, and the like.

As used herein, "alkynyl" refers to an alkyl group having one or more carbon-carbon triple bonds. Example alkynyl groups include ethynyl, propynyl, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. A heterocycloalkyl group having one or more fused aromatic rings can be attached through either the aromatic or non-aromatic portion. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "carboxy" refers to COOH.

As used herein, "carboxy alkyl ester" refers to —COO-(alkyl).

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "aminocarbonyl" refers to —$CONH_2$.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, or spectrophotometry (e.g., UV-visible); or by chromatography such as high performance liquid chromatography (HPLC) or thin layer chromatograpy (TLC).

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, et al., *Protective Groups in Organic Synthesis,* 3rd. Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, ▢,▢,▢-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atomosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in *Remington's Pharmaceutical Sciences*, 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 2-(4-Chlorophenyl)-N-(2-hydroxypropyl)acetamide (1-3)

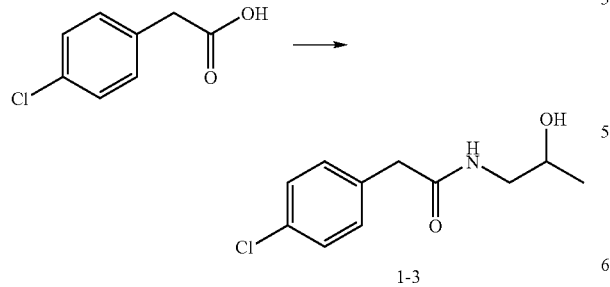

Method A (Boronic Acid)

Toluene (50 mL) was charged to a 3-neck round-bottom (500 mL) flask fitted with a Dean-Stark condenser. 4-Chlorophenylacetic acid (51.2 g, 300 mmol) was added, followed by 2,5,6-trifluorophenylboronic acid (30 mmol, 5.28 g) and 1-aminopropan-2-ol (24.8 g, 330 mmol) The reaction flask was heated at 120° C. for 23 h. The reaction mixture was cooled to room temperature, and then solvent was removed to afford the crude product as white solid. Then water (120 mL) was added to the crude product. The resulting product was filtered and dried in a vacuum oven overnight to yield 62.5 g of pure product as a white solid (91.5% yield).

Method B (Ketal)

To a 100 mL round-bottom flask equipped with a reflux condenser and a magnetic stirrer was charged 5 g (0.029 mol, 1.0 eq) of 2-(4-chlorophenyl)acetic acid and 0.279 g (1.5 mmol, 0.05 eq) p-toluenesulfonic acid (PTSA). Methanol (25 mL) was added to the flask followed by 3.4 mL (0.029 mol, 1.0 eq) of 2,2-dimethoxypropane (DMP). The resulting mixture was heated to reflux and held (about 4 h) until conversion to intermediate 2-(4-chlorophenyl)acetic acid methyl ester was greater than 95%. The methyl ester intermediate was not isolated.

Amino 2-propanol (7.3 mL, 0.06 mol, 3.1 eq) was then charged to the reaction mixture. Reflux was maintained with an internal temperature up to 90° C. until conversion to the title compound exceeded 98% by LC/MS. The reaction was complete within 12 h. Methanol was distilled off during the reaction. The reaction mixture was then charged with 30 mL (6.0 volumes) of water while maintaining the internal temperature around 100° C. followed by cooling in an ice bath for 30 minutes to precipitate the product as a fine solid. Solids were filtered and washed with 2×20 mL water and the wet cake was dried in a vacuum oven at 60° C. to yield 5.83 g of the title compound (87.4% yield) as white solids.

$^1$H NMR (400 MHz, DMSO d$_6$, δ): 8.06 (s, 1H), 7.38 (d, 2H), 7.30 (d, 2H), 4.71 (d, 1H), 3.64 (m, 1H), 3.45 (s, 2H), 3.02 (m, 2H), 1.02 (d, 3H).

LCMS: 455-457 (2M+H), 228-230 (MH), 210-212 (MH-H$_2$O), 125-127.

Example 2

Preparation of 2-(4-chlorophenyl)-N-(2-hydroxypropyl)acetamide (1-3) and 2-(4-chlorobenzyl)-5-methyl-4,5-dihydrooxazole (1-4)

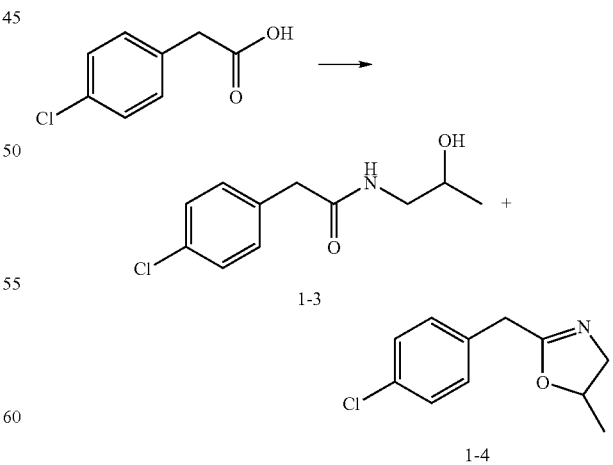

Isopropanol (100 mL) was charged to a 3-neck round-bottom flask (500 mL) followed by 4-chlorophenylacetic acid (8.6 g, 50.41 mmol) and 1-aminopropan-2-ol (3.78 g, 50.32 mmol). To this mixture was added 1-ethyl-3-(3-dimethylaminopropyl)-carbodiimide hydrochloride (EDC) (7.81 g, 50.41 mmol) and the resulting mixture was stirred at room temperature for 16 h. The reaction mixture was cooled and concentrated to afford crude product as a yellow oil. Then water (100 ml) and ethyl acetate were added to the crude product and the product isolated by extraction. The organic layer was washed with water (100 mL), dried over $Na_2SO_4$, filtered, and concentrated to yield a white solid (5 g, 43%).

Compound 1-3 (major)

LC/MS API 150 EX LC/MS, Prevail™ column C18, 5 μm, 4.6 mm/250 mm, 5 min run:

retention time: 1.68 min, gradient acetonitrile in water (0.01% TFA), 5-95%; 455-457 (2M+H), 228-230 (MH), 210-212 (MH-$H_2O$), 125-127.

Compound 1-4 (Minor)

LCMS API 150 EX LC/MS, Prevail™ column C18, 5 μm, 4.6 mm/250 mm, 5 min run:

retention time: 1.81 min, gradient acetonitrile in water (0.01% TFA), 5-95%; 210-212 (MH), 129, 125-127.

Example 3

Preparation of
1-(4-chlorophenethylamino)propan-2-ol (2-1)
hydrochloride salt

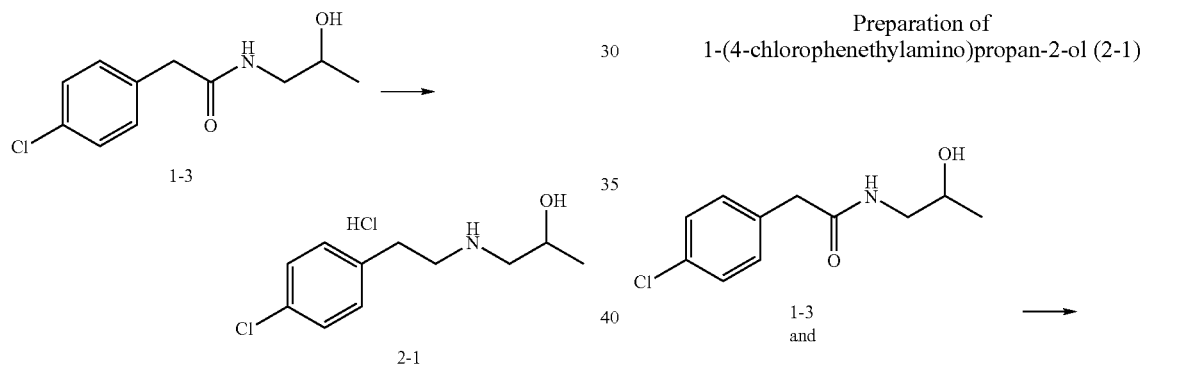

Method A

A 150 mL round bottom flask equipped with a condenser was charged with 10 g (0.044 mol, 1.0 eq) of 2-(4-chlorophenyl)-N-(2-hydroxypropyl)acetamide followed by 77 mL (0.154 moles, 3.5 eq) of 2.0 M $BH_3$/THF. Reaction contents foamed and were held for about 6 h at reflux until reaction completion exceeded 98% by LC/MS. Then 10 mL of methanol was added to the reaction mixture to quench excess borane with the first 4 mL of methanol resulting in fairly vigorous off-gassing. Solvent was distilled down to no less than about 20% of the initial volume and 100 mL of methanol was added followed by distillation down to an oil. The reaction vessel was then charged with 50 mL (5 volumes) of 37% HCl to precipitate a white solid which was filtered and dried in a vacuum oven at 70° C. to yield 8.25 g of white powder product as the HCl salt (75% yield).

Method B

To a 200 mL round bottom flask equipped with a condenser and a gas outlet leading to an aqueous sodium hypochlorite scrubber was charged 10 g (0.044 mol, 1.0 eq) of 2-(4-chlorophenyl)-N-(2-hydroxypropyl)acetamide followed by 77 mL of THF resulting in a clear solution. To the mixture was added dropwise 15.4 mL of 10.0 M (0.154 moles, 3.5 eq) of borane methyl sulfide complex resulting in violent foaming. The reaction was held at reflux until 98% reaction completion was verified by LCMS (~6 hr). White solid started to precipitate about two hours after borane addition had been completed. The reaction was quenched with 10 mL of methanol with the first 4 mL methanol resulting in vigorous off-gassing. The resulting mixture was then refluxed for ~1 h and then concentrated to about 20% of the original volume. Methanol (100 ml) was added, and the mixture was refluxed for ~1 h and then concentrated to a white solid residue. Conc. HCl (37%, 5 mL) was added to the residue at 0° C. (exothermic). The resulting mixture was filtered, and the filtered white solid was dried at 70° C. in a vacuum oven to constant weight (~5-7 h) then at room temperature overnight to afford crude product as a white solid 11.5 g (~104%). The solid was then partially dissolved in conc. HCl (20 mL). The resulting mixture was filtered to yield 0.87 g of white solid after drying. After adding ~5 mL water, the mother liquor precipitated additional white solid (7.87 g after drying) to give a combined yield of 8.74 g (80%).

$^1$H NMR (400 MHz, DMSO $d_6$, δ): 9.21 (s, 1H), 8.87 (s, 1H), 7.42 (d, 2H), 7.32 (d, 2H), 5.43 (d, 1H), 4.04 (m, 1H), 3.15 (m, 2H), 3.02 (m, 3H), 2.8 (m, 1H), 1.13 (d, 3H).

LCMS: 427-429 (2M+H), 214-216 (MH), 196-198 (MH-$H_2O$), 139-141.

Example 4

Preparation of
1-(4-chlorophenethylamino)propan-2-ol (2-1)

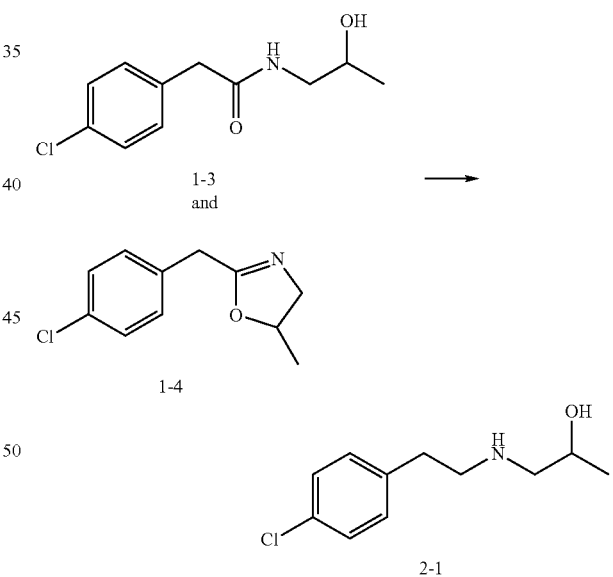

To a 50 mL round bottom flask equipped with a condenser was charged 1 g (4.4 mmol) of the mixture of 2-(4-chlorophenyl)-N-(2-hydroxypropyl)acetamide and 2-(4-chlorobenzyl)-5-methyl-4,5-dihydrooxazole produced in Example 2 followed by THF (10 mL) and 15.4 mL (15.4 mmol, 3.5 eq) of 1.0 M $BH_3$/THF. The reaction mixture was held at reflux for about 16 h until reaction completion exceeded 98% by LC/MS. The resulting mixture was distilled down to an oil, to which was added 5 mL (5 volumes) of 1 N NaOH with stirring for 1 h. Then 5 mL (5 volumes) of isopropyl acetate was added and the product isolated by extraction. The organic layer was washed with water, dried over Na$_2$SO$_4$, and concentrated to afford the product as a white solid (630 mg, 67%).

LCMS API 150 EX LC/MS, Prevail™ column C18, 5 μm, 4.6 mm/250 mm, 5 min run:

retention rime: 1.81 min, gradient acetonitrile in water (0.01% TFA), 5-95%; 427-429 (2M+H), 214-216 (MH), 196-198 (MH-H$_2$O), 139-141.

Example 5

Preparation of 2-chloro-N-(4-chlorophenethyl)propan-1-amine (3-1) hydrochloride

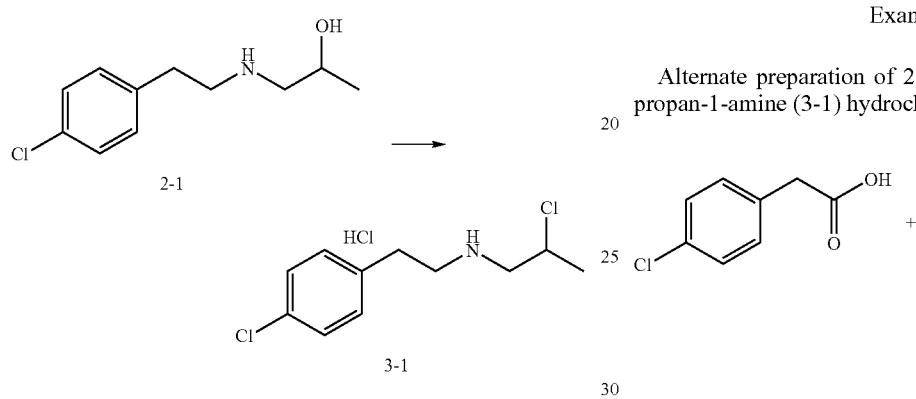

Method A

In a 25 mL 3-neck round bottom flask was suspended 1-(4-chlorophenethylamino)-propan-2-ol hydrochloride (2.088 g, 8.346 mmol) in 3.7 mL (1.85 vol) of toluene and N,N-dimethylacetamide (0.2346 mL, 2.504 mmol). The resulting milky white slurry was heated in an oil bath to 50° C. Under nitrogen blanket, the vessel was charged with thionyl chloride (0.7737 mL, 10.60 mmol) via syringe while the stirred reaction mixture was maintained between 50° C. and 60° C. The mixture became yellow during addition and then was heated to 60-65° C. for 2.5 hrs before being cooled to 15° C. The resulting beige sludge was suspended in 10 mL (5 vol) of toluene, suction filtered, and washed with 20 mL (10 vol) of toluene. The washed solid was sucked dry on the filter over 2.5 days. The light beige solids were transferred to a 50 mL round bottom flask and suspended in 4 mL (2 vol) of isopropyl alcohol (IPA) and 0.4 mL (0.2 vol) of water. The mixture was heated to reflux in an 87° C. oil bath and then allowed to cool to room temperature after 1 h. The mixture was then further cooled in an ice water bath to 10° C., held between 10° C. and 15° C. for 1.5 h, cooled in a salt/ice water bath (between 0° C. and 3° C.), and held at this temperature for an additional 1.5 h. The resulting slurry was suction filtered in a Buchner funnel, and the filtered solid was washed with a 15 mL IPA rinse of the crystallization flask. The resulting cake was sucked dry on the filter plate and then vacuum dried at 60° C. overnight to yield 1.924 g of final product as a white solid HCl salt (85.82% yield).

Method B

To a 15 mL 3-neck round bottom flask containing 1-(4-chlorophenethylamino)-propan-2-ol hydrochloride (1.254 g, 5.013 mmol) was added thionyl chloride (~0.7 mL) (slowly) via syringe to suspend solids. The mixture was then heated in an oil bath to 50° C. Additional thionyl chloride was then added for a total amount of 3.659 mL (50.13 mmol). The yellowish clear solution was heated to 62° C. in an oil bath and held at that temperature 2 h before being cooled to 17° C. in an ice water bath. The resulting slurry was suction filtered through a Buchner funnel, and the filtered solid was washed with IPA. The cake was vacuum dried at 60° C. (0.812 g, HPLC purity 99.87%). The mother liquor had a large amount of solid visible and was suction filtered in a Buchner funnel. The cake was washed with 10 mL of IPA and vacuum dried at 60° C. to yield an additional 0.124 g for a combined total of 0.936 g final product as the HCl salt (69.52% yield).

$^1$H NMR (400 MHz, DMSO d$_6$, δ): 9.55 (s, 1H), 9.15 (s, 1H), 7.42 (d, 2H), 7.32 (d, 2H), 4.58 (m, 1H), 3.45 (m, 2H), 3.25 (m, 2H), 3.02 (m, 2H), 1.56 (d, 3H).

LCMS: 232-234 (MH), 139-141, 103.

Example 6

Alternate preparation of 2-chloro-N-(4-chlorophenethyl)propan-1-amine (3-1) hydrochloride

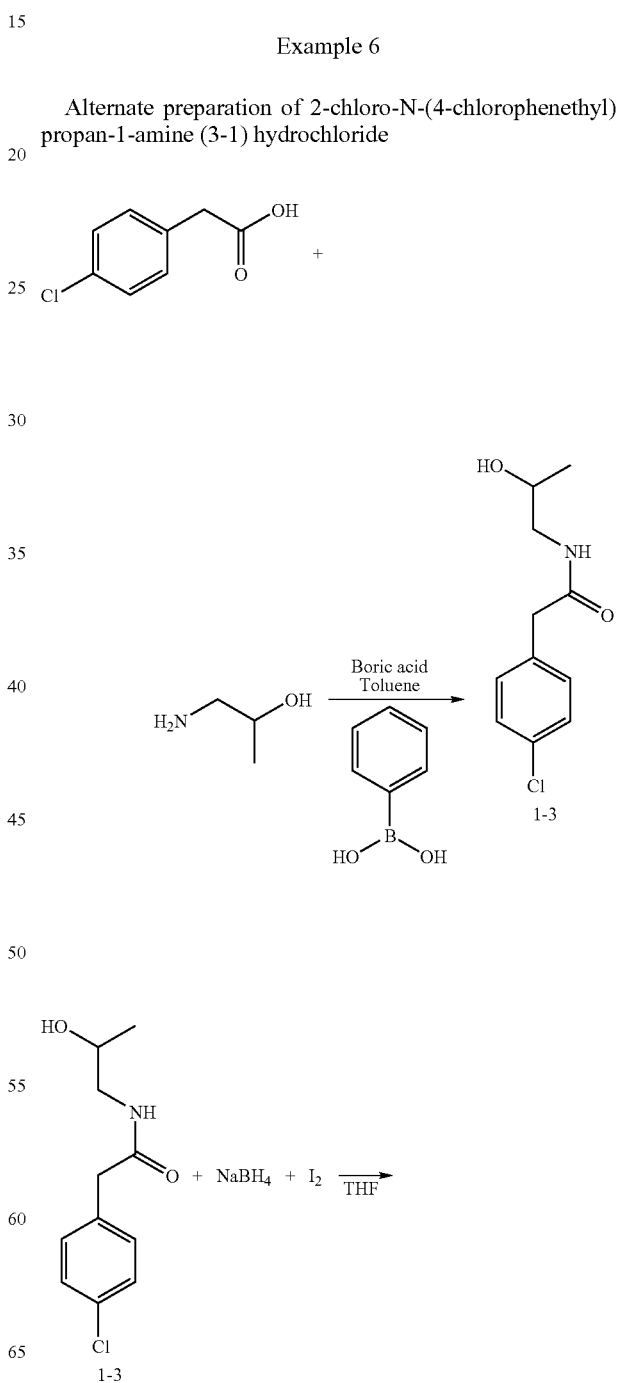

-continued

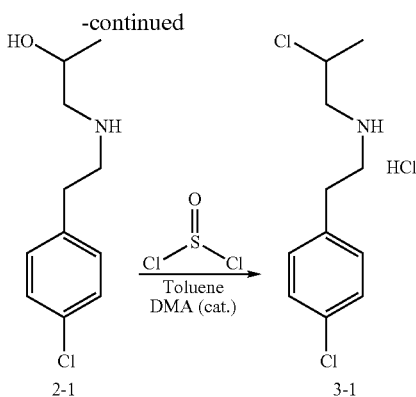

Step 1

2-(4-Chlorophenyl)acetic acid (1.9 kg, 11.1 mol, 1.00 eq), toluene (1 L), phenylboronic acid (67 g, 549 mmo, 0.049 eq.), and boric acid (68 g, 1.10 mol. 0.099 eq) where charged to a 20 L jacketed reactor in the specified order. After the resulting mixture had been heated with stirring to 40° C., 1-amino-2-propanol (908 g, 12.09 mol, 1.085 eq) and toluene (1 L) were added. The reaction mixture was then heated to reflux while the water coproduct was removed in a Dean-Stark trap. Refluxing and water removal were continued until conversion of 2-(4-chlorophenyl)acetic acid exceeded 98%. Such conversion is usually achieved with 8-12 hours of refluxing. Water coproduct removed in the Dean-Stark trap totaled 265 mL (14.72 mol). After the reaction mixture had been cooled to 60-70° C., 5 wt % aqueous sodium bicarbonate (2 L) was added slowly while the reaction mixture was maintained at 60-70° C. Water (10 mL) was then added slowly while the stirred reaction mixture was maintained at ≧50° C. The diluted reaction mixture was cooled to 30° C. and stirred at that temperature for 30 minutes. The resulting solid precipitate was filtered and vacuum dried for 48 hours at 50° C. to provide 2-(4-chlorophenyl)-N-(2-hydroxypropyl)acetamide (2.356 kg, 92.9% yield not corrected for purity, 90.12% purity by HPLC peak area).

Step 2

2-(4-Chlorophenyl)-N-(2-hydroxypropyl)acetamide (5.0 g, 21.96 mmol, 1.00 eq), tetrahydrofuran (THF, 7.5 mL), and sodium borohydride (1.662 g, 43.9 mmol, 2.00 eq) were charged to a 100 mL round bottomed flask. The resulting stirred white suspension was cooled to −10° C., and a solution of iodine (5.574 g, 21.96 mmol, 1.00 eq) in THF (10 mL) was added dropwise over 30 minutes while cooling of the reaction suspension was continued. Hydrogen gas evolved during the addition. After the addition, the dark brown reaction suspension was heated and stirred at 70° C. until 2-(4-chlorophenyl)-N-(2-hydroxypropyl)acetamide conversion was substantially complete. Such conversion was achieved in 3.5 hours at 70° C. The reaction mixture was cooled to 0° C., and methanol (15 mL) was added sufficiently slowly to maintain the stirred reaction mixture at about 0° C. with external cooling. The methanol addition was initially accompanied by fairly vigorous evolution of gas. After the resulting mixture had been heated at 65° C. for 0.5 hr, solvents were evaporated under vacuum. To the residual white slurry was added 50 wt % aqueous NaOH (15 mL, 286 mmol, 13 eq) while the stirred product mixture was maintained at 0° C. The resulting mixture was heated with stirring at 80° C. for 1.5 hr. After 0.5 hr of such heating, mild foaming stopped, and a mixture of two clear, homogenous layers was obtained. Toluene (20 mL) was added, and the resulting mixture was heated and stirred at 50° C. to extract the product into toluene. The lower aqueous layer was drained, and the upper organic layer was washed with water (two 15 mL portions). The washed organic layer was evaporated to dryness under vacuum at 60° C. Vacuum drying of the evaporation residue at 60° C. was continued for 2 hr to yield intermediate 1-(4-chlorophenethylamino)-propan-2-ol as an off-white solid (4.23 g, 90.1% yield, 96.17% purity by HPLC peak area). To the intermediate 1-(4-chlorophenethylamino)propan-2-ol in a round bottomed flask was added toluene (20 mL). (One skilled in the art can achieve substantially the same water-free mixture of intermediate 1-(4-chlorophenethylamino)propan-2-ol in toluene by azeotropic removal of water without evaporation of the majority of the toluene.)

N,N-Dimethylacetamide (DMA), 0.614 mL, 6.60 mmol, 0.301 eq) was added to the substantially water-free mixture of intermediate 1-(4-chlorophenethylamino)propan-2-ol in toluene as it was stirred under nitrogen at 40-45° C. Thionyl chloride (2.04 mL, 28.0 mmol, 1.274 eq) was then added while the stirred mixture was maintained at 50-60° C. The stirred reaction mixture was then heated at 62° C. for three hours. LC/MS analysis of the crude reaction mixture indicated that conversion of the intermediate 1-(4-chlorophenethyl-amino)propan-2-ol was substantially complete after two hours. After the reaction mixture had been cooled to 0-5° C., isopropanol (5 mL) was added while the stirred product mixture was maintained at 0-5° C. Stirring at that temperature was continued for 2-3 hours, and then toluene (5 mL) was added to the suspension. After the resulting mixture had been heated to 60° C. for 30 minutes, the solid product was recovered by filtration, washing with isopropanol (2×5 mL), and vacuum drying at 72° C. overnight to provide off-white solid 2-chloro-N-(4-chlorophenethyl)propan-1-amine hydrochloride (4.38 g, 74.3% yield, 99.60% purity by HPLC peak area).

Example 7

Preparation of (R,S)-8-chloro-1-methyl-2,3,4,5-tetrahydro-1H-3-benzazepine (3-2)

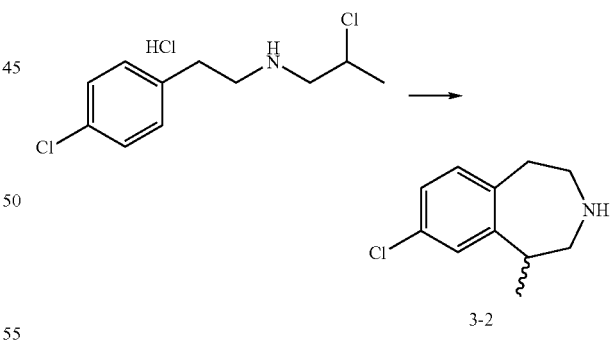

To a reactor equipped with an overhead stirrer, jacket temperature control, a nitrogen inlet, and a caustic scrubber vent were charged, in the specified order, 2-chloro-N-(4-chlorophenethyl)propan-1-amine hydrochloride (1.00 Kg, 3.72 mol, 1.00 equiv.), aluminum chloride (0.745 Kg, 5.58 mol, 1.50 equiv.), and 1,2-dichlorobenzene (2.88 Kg). The stirred reactor contents were heated to 125-130° C., and stirring was continued at that temperature for 14-18 h. At 60-70° C., a dark colored solution was obtained. After reaction completion (<1.0% starting material by HPLC peak area) had been verified, the stirred reactor contents were cooled to 30-35° C.

To a second reactor, vented to a caustic scrubber, was charged purified water (1.60 L) and silica gel (0.160 Kg). The Friedel Crafts reaction mixture was transferred from the first reactor to the second reactor sufficiently slowly to maintain the stirred contents of the second reactor at <60° C. The silica gel was filtered on a medium to coarse filter element at 55-60° C., and the filtered solids were subsequently washed with purified water (800 mL) preheated to 50-60° C. The combined mother and wash liquor filtrates were cooled to 20-25° C. with vigorous agitation. Then the stirring was stopped, and the phases were allowed to separate at 20-25° C. (Process volume peaked at this point at 5.68 L). Three phases separated after 1-2 h of standing. The lowest layer was drained to waste disposal. This dark layer consisted mostly of 1,2-dichlorobenzene (1.64 Kg, 1.33 L) at pH 3-4. About 1% of the product was lost to this layer. The remaining two phases were allowed to stand without agitation for another 2-4 h. The lower layer was drained and saved (Layer A). This light colored phase (2.64 Kg, 2.00 L, pH 2-3) contained ~90% 8-chloro-1-methyl-2,3,4,5-tetrahydro-1H-3-benzazepine. The upper layer (2.24 Kg of a turbid water phase at pH 0-1) contained ~1-4% 8-chloro-1-methyl-2,3,4,5-tetrahydro-1H-3-benzazepine and remained in the reactor for back-extraction.

The reactor was charged with cyclohexane (1.10 Kg) and then 30% aqueous NaOH (2.44 Kg, 18.3 mol, 4.91 equiv.). The resulting mixture (5.60 L) was stirred vigorously for 30 minutes at room temperature. The stirring was stopped, and the phases were allowed to separate for 25-40 minutes. If the pH of the lower (aqueous) phase was it was drained to waste disposal. Otherwise, more 30% aqueous NaOH was added, and this extraction was repeated. At pH 14, the aqueous phase contained <0.1% 8-chloro-1-methyl-2,3,4,5-tetrahydro-1H-3-benzazepine free base. The remaining upper (organic) phase from the reactor was drained and saved (Layer B). The reactor was rinsed with purified water and followed by a suitable organic solvent to remove residual salts. The lower, light-colored product phase (the middle of the original three phases, Layer A) and the upper phase (organic, Layer B) were returned to the reactor. To the stirred reactor contents was added 30% aqueous NaOH (1.60 Kg, 12.0 mol, 3.23 eq.). The reactor contents were stirred vigorously for 0.5 h. The stirring was discontinued and the phases were allowed to separate over 15-30 min. The lower (aqueous) layer was drained to waste disposal. To the upper (organic) phase remaining in the reactor was added purified water (2.40 Kg). The reactor contents were stirred vigorously at 60-65° C. for 0.5 h. The stirring was discontinued, and the phases were allowed to separate at 60-65° C. over 1.5-2 h. The lower (aqueous) layer was drained to waste disposal. With a reactor jacket temperature of 55-60° C., solvent from the upper (organic) layer was removed by vacuum distillation at pressures starting at 115-152 torr and falling to 40 ton. The crude product, 8-chloro-1-methyl-2,3,4,5-tetrahydro-1H-3-benzazepine as the free base, was obtained as a yellow to brown, oily distillation residue.

Example 8

Preparation of L-(+)-tartaric acid salt of (R)-8-chloro-1-methyl-2,3,4,5-tetrahydro-1H-3-benzazepine (3-3)

The distillation residue (crude 8-chloro-1-methyl-2,3,4,5-tetrahydro-1H-3-benzazepine as the free base from Example 7 was dissolved in acetone (0.400 kg). The resulting solution was drained and weighed to assay the 8-chloro-1-methyl-2,3,4,5-tetrahydro-1H-3-benzazepine content by HPLC. Results of the assay were used to calculate charges of acetone, L-tartaric acid, and water. The quantities indicated below are typical for achievement of the target 8-chloro-1-methyl-2,3,4,5-tetrahydro-1H-3-benzazepine: acetone: L-tartaric acid: water mole ratio of 1.00:9.6:0.25:3.6 prior to addition of seed crystals. More acetone (1.415 Kg) was added to the reactor and the stirred reactor contents were heated to 47-52° C. To the resulting solution was added a solution of L-tartaric acid (0.1223 kg, 0.815 mol, 0.219 equiv.) in purified water (0.211 kg) at a steady rate over 5-15 minutes. A thin suspension formed during the addition but then redissolved when the mixture temperature was reestablished at 50° C. Hemitartrate seed crystals (0.80 g) were added to the 50° C. solution to initiate nucleation. Nucleation was allowed to continue for 2-3 h with agitation at 47-52° C. Acetone (0.473 kg) was added to the reactor while the stirred reactor contents were maintained at 50° C. The resulting suspension was cooled to 0-5° C. slowly over 3-5 h. Stirring was continued at 0° C. for another 1-3 h. The resulting white precipitate was collected on a medium to fine filter element and then washed with a mixture of acetone (0.900 kg) and purified water (0.054 kg). The enantiomeric excess (ee) of the wet cake was determined.

If the ee was <98%, the wet cake was transferred back into the reactor and reslurried in a mixture of acetone (1.90 kg) and purified water (0.400 kg) at 55-60° C. for 0.5-1 h. If dissolution had not been achieved after one hour, then water (approximately 0.160 kg) was added until a clear solution was achieved. The resulting mixture was then cooled to 0-5° C. slowly over 2-3 h. Stirring at 0° C. was continued for another 3-5 h. The resulting white precipitate was collected on a medium to fine filter element and then washed with acetone (0.400 kg) at 0-° C.

The washed solid product (296 g wet) was dried at 60-65° C. for 15-20 h. The yield of 8-chloro-1-methyl-2,3,4,5-tetrahydro-1H-3-benzazepinium hemitartrate, with about 99.7% ee and 7.5 wt. % water content, was 295 g (27.1% based on racemic 2-chloro-N-4-chlorophenethyl)propan-1-amine hydrochloride and corrected for product water content).

Example 9

Preparation of hydrochloric acid salt of (R)-8-chloro-1-methyl-2,3,4,5-tetrahydro-1H-3-benzazepine (3-5)

To a reactor equipped with an overhead stirrer and a nitrogen inlet was charged, in the specified order, 8-chloro-1-methyl-2,3,4,5-tetrahydro-1H-3-benzazepinium hemitartrate (1.00 kg containing 7.5 wt % water, 1.71 mol, 0.500 eq), potassium carbonate (0.508 kg, 3.68 mol, 1.076 eq), ethyl acetate (2.68 kg), and purified water (2.68 kg). The resulting mixture was stirred at 20-25° C. for 30-40 min, and then the phases were allowed to separate over 0.5-1 h. The lower (aqueous) phase was drained to waste disposal. Purified water (2.68 kg) was added to the reactor, and the resulting mixture was vigorously stirred for 10-20 min. The phases were allowed to separate over 1-1.5 h. The lower (aqueous) phase was drained to waste disposal. With the reactor contents at a temperature of 40-45° C., the solvent was removed by vacuum distillation at pressures falling from 153 torr to 46 torr. The residue was cooled to 20-25° C. Ethyl acetate (3.81 kg) was charged to the reactor, and the distillation residue was dissolved with stirring. The water content of the resulting solution was verified by Karl Fischer analysis to be <0.8 wt. %. The solution was filtered through a polishing filter. The reactor was rinsed through the filter with ethyl acetate (2.33 kg) previously verified by Karl Fischer analysis to have <0.05 wt. % water content. Both the solution and rinse filtrates were charged back into the reactor. Purified water (39.9 g) was added to the reactor. The stirred reactor contents were cooled to 0-5° C., and then HCl gas (19.0 g, 0.521 mol, 0.153 eq) was added while the stirred reactor contents were maintained at 0-5° C. (R)-8-chloro-1-methyl-2,3,4,5-tetrahydro-1H-3-benzazepine hemihydrate seed crystals (1.33 g) were added to the stirred reactor contents to initiate nucleation at 0-5° C. HCl gas (107.6 g, 2.95 mol, 0.864 eq) was charged to the reactor at a steady rate over at least 1.5-2 h while the stirred reactor contents were maintained at 0-5° C. The resulting suspension was stirred at 0-5° C. for 2 hours. The resulting white precipitate was collected on a medium to fine filter element. The reactor and then the filtered solid product were washed with ethyl acetate (1.33 kg). The wet cake (ca. 867 g) was dried under reduced pressure and 33-37° C. for 20 h or until the cake temperature had been stable for 4 h, whichever occurred first. The resulting (R)-8-chloro-1-methyl-2,3,4,5-tetrahydro-1H-3-benzazepine hemihydrate hydrochloride (3.7 wt. % water content, 14.7% chloride content, <0.01% ROI, >99.6% ee, >99% HPLC purity, and <0.1% wrong isomer content) was obtained in a yield of about 741 g (89.9%).

Various modifications of the invention, in addition to those described herein, will be apparent to those skilled in the art from the foregoing description. Such modifications are also intended to fall within the scope of the appended claims. Each reference, including all patents, patent applications, and publications, cited in the present application is incorporated herein by reference in its entirety.

What is claimed is:

1. A process for preparing an amide compound of Formula 1-3:

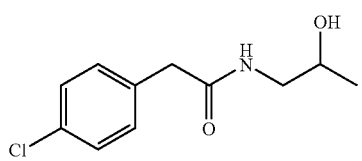

comprising reacting a phenylacetic acid derivative compound of Formula 1-1:

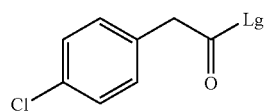

or salt thereof, wherein Lg is a leaving group, with an amine compound of Formula 1-2:

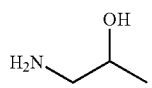

or salt thereof, in the presence of a coupling reagent to afford said amide compound of Formula 1-3.

2. The process according to claim 1, wherein Lg is OH.
3. The process according to claim 2, wherein said coupling reagent comprises phenylboronic acid, boric acid, or mixture thereof.
4. The process according to claim 2, wherein said coupling reagent comprises 2,5,6-trifluorophenylboronic acid.
5. The process according to claim 2, wherein said coupling reagent comprises a boron-containing acid, a carbodiimide, or a ketal.
6. The process according to claim 5, wherein said carbodiimide is 1-ethyl-3-(3-dimethylaminopropyl)-carbodiimide hydrochloride (EDC).
7. The process according to claim 5, wherein said ketal has the formula:

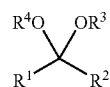

wherein $R^1$, $R^2$, $R^3$, and $R^4$ are $C_{1-6}$ alkyl.
8. The process according to claim 7, wherein $R^1$, $R^2$, $R^3$, and $R^4$ are independently selected from methyl and ethyl.
9. The process according to claim 7, wherein said ketal comprises 2,2-dimethoxypropane.
10. The process according to claim 7, wherein said reacting is carried out in the presence of an acid catalyst.
11. The process according to claim 10, wherein said catalyst comprises a sulfonic acid.
12. The process according to claim 10, wherein said catalyst comprises an optionally substituted arylsulfonic acid.
13. The process according to claim 10, wherein said catalyst comprises p-toluenesulfonic acid.
14. The process according to claim 1, wherein Lg is halo.
15. The process according to claim 14, wherein said coupling reagent comprises a base.
16. The process according to claim 15, wherein said base comprises a tri($C_{1-6}$)alkylamine.
17. The process according to claim 15, wherein said base is triethylamine.
18. The process according to claim 1, further yielding a dihydrooxazole compound of Formula 1-4:

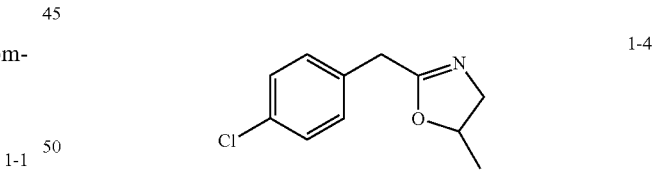

or salt thereof.
19. The process according to claim 1, wherein said reacting is carried out in the presence of a solvent.
20. The process according to claim 19, wherein said solvent is an aromatic solvent or an alcohol solvent.
21. The process according to claim 19, wherein said solvent comprises toluene.
22. The process according to claim 19, wherein said solvent comprises methanol, ethanol, or isopropanol.
23. The process according to claim 1, wherein said reacting is carried out at about room temperature.
24. The process according to claim 1, wherein said reacting is carried out at elevated temperature.
25. The process according to claim 24, wherein said elevated temperature is about 80° C. to about 140° C.

26. A process for preparing an amide compound of Formula 1-3:

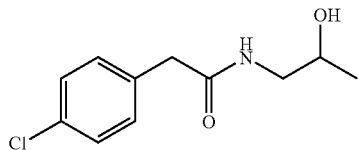

comprising reacting, in a solvent comprising toluene and at elevated temperature, a phenylacetic acid derivative compound of Formula 1-1:

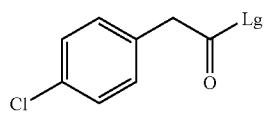

or salt thereof, wherein Lg is OH, with an amine compound of Formula 1-2:

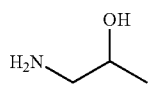

or salt thereof, in the presence of at least one boron-containing acid to afford said amide compound of Formula 1-3.

27. The process according to claim 26, wherein said reacting is carried out in the presence of phenylboronic acid, boric acid, or mixture thereof.

28. The process according to claim 26, wherein said reacting is carried out in the presence of 2,5,6-trifluorophenylboronic acid.

29. A process for preparing an amide compound of Formula 1-3:

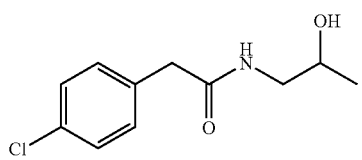

comprising reacting, in a solvent comprising isopropyl alcohol and at about room temperature, a phenylacetic acid derivative compound of Formula 1-1:

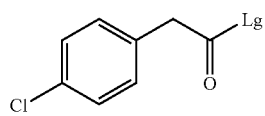

or salt thereof, wherein Lg is OH, with an amine compound of Formula 1-2:

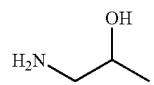

or salt thereof, in the presence of 1-ethyl-3-(3-dimethylaminopropyl)-carbodiimide hydrochloride to afford said amide compound of Formula 1-3.

30. The process according to claim 29, further affording a dihydrooxazole compound of Formula 1-4:

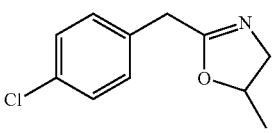

or salt thereof.

31. A process for preparing an amide compound of Formula 1-3:

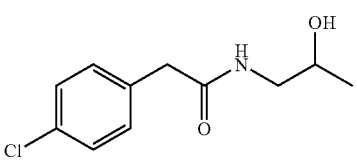

comprising reacting, in an alcohol solvent and optionally in the presence of an acid catalyst, a phenylacetic acid derivative compound of Formula 1-1:

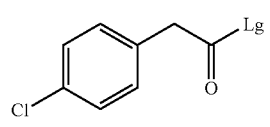

or salt thereof, wherein Lg is OH, with an amine compound of Formula 1-2:

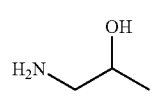

or salt thereof, in the presence of 2,2-dimethoxypropane to afford said amide compound of Formula 1-3.

32. The process according to claim 31 further affording a dihydrooxazole compound of Formula 1-4:

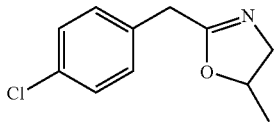

or salt thereof.

33. The process according to claim 31 further comprising combining said 2,2-dimethoxypropane with said phenylacetic acid derivative compound of Formula 1-1, or salt thereof, prior to said reacting with said amine compound of Formula 1-2, or salt thereof.

34. The process according to claim 31, wherein said combining affords 2-(4-chlorophenyl)acetic acid methyl ester.

35. The process according to claim 32, wherein said combining is carried out at elevated temperature.

36. The process according to claim 35, wherein said elevated temperature is about 60° C. to about 120° C.

37. The process according to claim 34, wherein conversion of said phenylacetic acid derivative compound of Formula 1-1, or salt thereof, to said 2-(4-chlorophenyl)acetic acid methyl ester is about 90% or greater.

38. A process for preparing an amino alcohol compound of Formula 2-1:

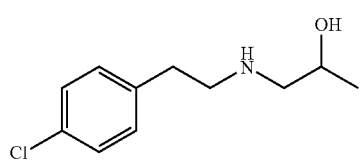

or salt thereof, comprising reacting an amide compound of Formula 1-3:

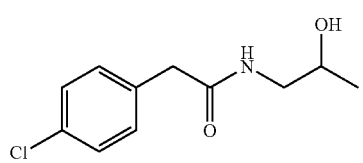

with a reducing agent to afford said amino alcohol compound of Formula 2-1, or salt thereof.

39. The process according to claim 38 further comprising reacting a dihydrooxazole compound of Formula 1-4:

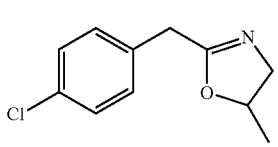

or salt thereof, with said reducing agent.

40. The process according to claim 38, wherein said reducing agent comprises a borane, dialkylborane, alkali metal trialkylboron hydride, alkali metal aluminum hydride, alkali metal borohydride, alkali metal trialkoxyaluminum hydride, dialkylaluminum hydride, or $H_2$ optionally in the presence of a catalyst.

41. The process according to claim 38, wherein said reducing agent comprises $BH_3$.

42. The process according to claim 41, wherein said $BH_3$ is generated in situ.

43. The process according to claim 38, wherein said reducing agent comprises a borane tetrahydrofuran complex.

44. The process according to claim 38, wherein said reducing agent comprises a borane methylsulfide complex.

45. The process according to claim 38, wherein said reducing agent is provided in molar excess relative to the amount of said amide compound of Formula 1-3.

46. The process according to claim 38, wherein the molar ratio of said reducing agent to said amide compound of Formula 1-3 is about 1:1 to about 10:1.

47. The process according to claim 38, wherein the molar ratio of said reducing agent to said amide compound of Formula 1-3 is about 1:1 to about 5:1.

48. The process according to claim 38, wherein the molar ratio of said reducing agent to said amide compound of Formula 1-3 is about 3.5:1.

49. The process according to claim 38, wherein said reducing agent comprises $NaBH_4$ in the presence of iodine.

50. The process according to claim 49, wherein the molar ratio of $NaBH_4$ to iodine to said amide compound of Formula 1-3 is about 10:1:1.

51. The process according to claim 49, wherein the molar ratio of $NaBH_4$ to iodine to said amide compound of Formula 1-3 is about 5:1:1.

52. The process according to claim 49, wherein the molar ratio of $NaBH_4$ to iodine to said amide compound of Formula 1-3 is about 2.5:1:1.

53. The process according to claim 38, wherein said reacting is carried out at elevated temperature.

54. The process of claim 53, wherein said elevated temperature is about 30° C. to about 80° C.

55. The process of claim 53, wherein said elevated temperature is about 40° C. to about 70° C.

56. The process of claim 53, wherein said elevated temperature is about 50° C. to about 60° C.

57. The process according to claim 38, wherein conversion of said amide compound of Formula 1-3 to said amino alcohol compound of Formula 2-1, or salt thereof, is about 90% or greater.

58. The process according to claim 38, wherein said amide compound of Formula 1-3 is prepared by the process of claim 1.

59. A process for preparing an amino alcohol compound of Formula 2-1:

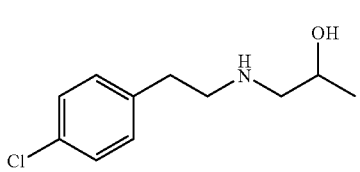

or salt thereof, comprising:

a) reacting a phenylacetic acid derivative compound of Formula 1-1:

[Structure 1-1: 4-chlorophenylacetyl-Lg]

or salt thereof, wherein Lg is a leaving group, with an amine compound of Formula 1-2:

[Structure 1-2: H₂N-CH₂-CH(OH)-CH₃]

or salt thereof, in the presence of a coupling reagent to afford an amide compound of Formula 1-3 and optionally a dihydrooxazole compound of Formula 1-4, or salt thereof:

[Structure 1-3]

[Structure 1-4]

and b) reacting said amide compound of Formula 1-3 and optionally said dihydrooxazole compound of Formula 1-4, or salt thereof, with a reducing agent to afford said amino alcohol compound of Formula 2-1, or salt thereof.

60. A compound of Formula 1-3:

[Structure 1-3]

61. The compound of claim 60 that is substantially isolated.

62. A compound of Formula 1-4:

[Structure 1-4]

or salt thereof.

63. The compound of claim 62, or salt thereof, that is substantially isolated.

64. A composition comprising a compound of claim 60 or 62, or salt thereof.

65. A composition comprising a compound of Formula 1-3 and a compound of Formula 1-4, or salt thereof:

[Structure 1-3]

[Structure 1-4]

66. A process for preparing a compound of Formula 3-5:

[Structure 3-5: NH·HCl·0.5 H₂O]

comprising:

a) reacting a phenylacetic acid derivative compound of Formula 1-1:

[Structure 1-1]

or salt thereof, wherein Lg is a leaving group, with an amine compound of Formula 1-2:

[Structure 1-2]

or salt thereof, in the presence of a coupling reagent to afford an amide compound of Formula 1-3 and optionally a dihydrooxazole compound of Formula 1-4, or salt thereof:

[Structure 1-3]

-continued

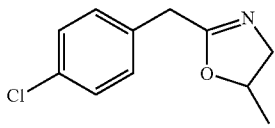

1-4 b) reacting said amide compound of Formula 1-3 and optionally said dihydrooxazole compound of Formula 1-4, or salt thereof, with a reducing agent to afford an amino alcohol compound of Formula 2-1:

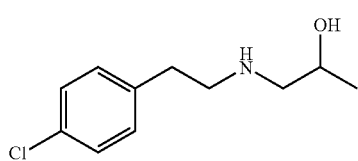

2-1 or salt thereof;

c) reacting said amino alcohol compound of Formula 2-1, or salt thereof, with a chlorinating reagent to afford a dichloro compound of Formula 3-1:

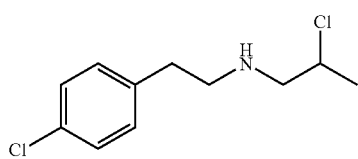

3-1 or salt thereof;

d) reacting said dichloro compound of Formula 3-1 with a cyclizing reagent to afford a 3-benzazepine compound of Formula 3-2:

3-2 e) contacting said 3-benzazepine compound of Formula 3-2 with L-(+)-tartaric acid to afford a tartrate salt of Formula 3-3:

3-3 f) reacting said tartrate salt of Formula 3-3 with a base to afford the optically active compound of Formula 3-4:

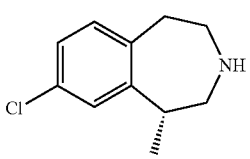

3-4 and g) reacting said optically active compound of Formula 3-4 with HCl to afford said compound of Formula 3-5.

* * * * *